(12) United States Patent
Pal

(10) Patent No.: US 8,945,169 B2
(45) Date of Patent: Feb. 3, 2015

(54) EMBOLIC PROTECTION DEVICE

(75) Inventor: Dharmendra Pal, Wilmington, MA (US)

(73) Assignee: Cook Medical Technologies LLC, Bloomington, IN (US)

( * ) Notice: Subject to any disclaimer, the term of this patent is extended or adjusted under 35 U.S.C. 154(b) by 1001 days.

(21) Appl. No.: 11/375,328

(22) Filed: Mar. 14, 2006

(65) Prior Publication Data

US 2006/0223386 A1    Oct. 5, 2006

Related U.S. Application Data

(60) Provisional application No. 60/661,731, filed on Mar. 15, 2005.

(51) Int. Cl.
*A61M 29/00* (2006.01)
*A61F 2/01* (2006.01)

(52) U.S. Cl.
CPC ............ *A61F 2/013* (2013.01); *A61F 2002/018* (2013.01); *A61F 2230/0006* (2013.01); *A61F 2230/0067* (2013.01)
USPC .......................................... 606/200; 606/192

(58) Field of Classification Search
USPC ........................................................ 606/200
See application file for complete search history.

(56) References Cited

U.S. PATENT DOCUMENTS

| | | | |
|---|---|---|---|
| 3,108,593 A | 10/1963 | Glassman | |
| 3,334,629 A | 8/1967 | Cohn | |
| 3,472,230 A | 10/1969 | Fogarty | |
| 3,547,103 A | 12/1970 | Cook | |
| 3,635,223 A | 1/1972 | Klieman | |
| 3,923,065 A | 12/1975 | Nozick et al. | |
| 3,952,747 A | 4/1976 | Kimmell, Jr. | |
| 3,978,863 A | 9/1976 | Fettel et al. | |
| 3,996,938 A | 12/1976 | Clark, III | |
| 4,425,908 A | 1/1984 | Simon | |
| 4,456,000 A | 6/1984 | Schjeldahl et al. | |
| 4,494,531 A | 1/1985 | Gianturco | |
| 4,548,206 A | 10/1985 | Osborne | |
| 4,561,439 A | 12/1985 | Bishop et al. | |
| 4,562,039 A | 12/1985 | Koehler | |
| 4,604,094 A | 8/1986 | Shook | |

(Continued)

FOREIGN PATENT DOCUMENTS

| | | |
|---|---|---|
| DE | 3429850 A1 | 2/1986 |
| EP | 1127556 A2 | 8/2001 |

(Continued)

OTHER PUBLICATIONS

Grummon, David S. et al., Appl. Phys. Lett., 82, 2727 (2003), pp. 2727.

(Continued)

*Primary Examiner* — Darwin Erezo
*Assistant Examiner* — Richard Louis
(74) *Attorney, Agent, or Firm* — Brinks Gilson & Lione

(57) ABSTRACT

An embolic protection device is provided for deployment within a body vessel to collect embolic debris there from. The device includes a filter for collecting the embolic debris and a frame for supporting the filter. The frame generally defines a closed loop that has a collapsed state and an opened state. Furthermore, the frame includes a tube portion that receives an opening means to open the closed loop from the collapsed state to the opened state.

21 Claims, 7 Drawing Sheets

(56) References Cited

U.S. PATENT DOCUMENTS

| | | | |
|---|---|---|---|
| 4,619,246 | A | 10/1986 | Molgaard-Nielsen et al. |
| 4,643,184 | A | 2/1987 | Mobin-Uddin |
| 4,646,736 | A | 3/1987 | Auth |
| 4,650,472 | A | 3/1987 | Bates |
| 4,665,906 | A | 5/1987 | Jervis |
| 4,669,464 | A | 6/1987 | Sulepov |
| 4,688,553 | A | 8/1987 | Metals |
| 4,723,549 | A | 2/1988 | Wholey et al. |
| 4,727,873 | A | 3/1988 | Mobin-Uddin |
| 4,732,152 | A | 3/1988 | Wallsten et al. |
| 4,817,600 | A | 4/1989 | Herms et al. |
| 4,824,435 | A | 4/1989 | Giesy et al. |
| 4,832,055 | A | 5/1989 | Palestrant |
| 4,846,794 | A | 7/1989 | Hertzer |
| 4,848,343 | A | 7/1989 | Wallsten et al. |
| 4,873,978 | A | 10/1989 | Ginsburg |
| 4,943,297 | A | 7/1990 | Saveliev et al. |
| 4,957,501 | A | 9/1990 | Lahille et al. |
| 4,990,156 | A | 2/1991 | Lefebvre |
| 4,998,916 | A | 3/1991 | Hammerslag et al. |
| 5,053,008 | A | 10/1991 | Bajaj |
| 5,059,205 | A | 10/1991 | El-Nounou et al. |
| 5,069,226 | A | 12/1991 | Yamauchi et al. |
| 5,078,726 | A | 1/1992 | Kreamer |
| 5,100,423 | A | 3/1992 | Fearnot |
| 5,108,418 | A | 4/1992 | Lefebvre |
| 5,108,419 | A | 4/1992 | Reger et al. |
| 5,112,347 | A | 5/1992 | Taheri |
| 5,129,890 | A | 7/1992 | Bates et al. |
| 5,129,910 | A | 7/1992 | Phan et al. |
| 5,133,733 | A | 7/1992 | Rasmussen et al. |
| 5,147,379 | A | 9/1992 | Sabbaghian et al. |
| 5,152,777 | A | 10/1992 | Goldberg |
| 5,160,342 | A | 11/1992 | Reger |
| 5,163,927 | A | 11/1992 | Woker et al. |
| 5,203,772 | A | 4/1993 | Hammerslag et al. |
| 5,234,458 | A | 8/1993 | Metais |
| 5,242,462 | A | 9/1993 | El-Nounou |
| 5,243,996 | A | 9/1993 | Hall |
| 5,251,640 | A | 10/1993 | Osborne |
| 5,263,964 | A | 11/1993 | Purdy |
| 5,300,086 | A | 4/1994 | Gory et al. |
| 5,324,304 | A | 6/1994 | Rasmussen |
| 5,329,942 | A | 7/1994 | Gunther et al. |
| 5,344,427 | A | 9/1994 | Cottenceau et al. |
| 5,350,397 | A | 9/1994 | Palermo et al. |
| 5,350,398 | A | 9/1994 | Pavcnik et al. |
| 5,364,345 | A | 11/1994 | Lowery et al. |
| 5,370,657 | A | 12/1994 | Irie |
| 5,375,612 | A | 12/1994 | Cottenceau et al. |
| 5,383,887 | A | 1/1995 | Nadal |
| 5,413,586 | A | 5/1995 | Dibie et al. |
| 5,415,630 | A | 5/1995 | Gory et al. |
| 5,417,708 | A | 5/1995 | Hall et al. |
| 5,451,233 | A | 9/1995 | Yock |
| 5,458,573 | A | 10/1995 | Summers |
| 5,522,881 | A | 6/1996 | Lentz |
| 5,527,338 | A | 6/1996 | Purdy |
| 5,531,788 | A | 7/1996 | Dibie et al. |
| 5,549,551 | A | 8/1996 | Peacock et al. |
| 5,549,626 | A | 8/1996 | Miller et al. |
| 5,556,414 | A | 9/1996 | Turi |
| 5,562,698 | A | 10/1996 | Parker |
| 5,571,135 | A | 11/1996 | Fraser et al. |
| 5,591,195 | A | 1/1997 | Taheri et al. |
| 5,601,595 | A | 2/1997 | Smith |
| 5,624,461 | A | 4/1997 | Mariant |
| 5,626,605 | A | 5/1997 | Irie et al. |
| 5,630,797 | A | 5/1997 | Diedrich et al. |
| 5,634,942 | A | 6/1997 | Chevillon et al. |
| 5,649,953 | A | 7/1997 | Lefebvre |
| 5,662,703 | A | 9/1997 | Yurek et al. |
| 5,669,933 | A | 9/1997 | Simon et al. |
| 5,681,347 | A | 10/1997 | Cathcart et al. |
| 5,690,642 | A | 11/1997 | Osborne et al. |
| 5,690,667 | A | 11/1997 | Gia |
| 5,693,067 | A | 12/1997 | Purdy |
| 5,693,087 | A | 12/1997 | Parodi |
| 5,695,518 | A | 12/1997 | Laerum |
| 5,695,519 | A | 12/1997 | Summers et al. |
| 5,700,253 | A | 12/1997 | Parker |
| 5,709,704 | A | 1/1998 | Nott et al. |
| 5,713,853 | A | 2/1998 | Clark et al. |
| 5,720,764 | A | 2/1998 | Naderlinger |
| 5,725,550 | A | 3/1998 | Nadal |
| 5,738,667 | A | 4/1998 | Solar |
| 5,746,767 | A | 5/1998 | Smith |
| 5,755,772 | A | 5/1998 | Evans et al. |
| 5,755,790 | A | 5/1998 | Chevillon et al. |
| 5,766,203 | A | 6/1998 | Imran et al. |
| 5,769,816 | A * | 6/1998 | Barbut et al. ............... 604/93.01 |
| 5,769,871 | A | 6/1998 | Mers et al. |
| 5,795,322 | A | 8/1998 | Boudewijn |
| 5,800,457 | A | 9/1998 | Gelbfish et al. |
| 5,800,525 | A | 9/1998 | Bachinski et al. |
| 5,810,874 | A | 9/1998 | Lefebvre |
| 5,814,027 | A | 9/1998 | Hassett et al. |
| 5,814,064 | A * | 9/1998 | Daniel et al. .................. 606/200 |
| 5,820,592 | A | 10/1998 | Hammerslag |
| 5,827,324 | A | 10/1998 | Cassell et al. |
| 5,830,230 | A | 11/1998 | Berryman et al. |
| 5,836,968 | A | 11/1998 | Simon et al. |
| 5,836,969 | A | 11/1998 | Kim et al. |
| 5,846,260 | A | 12/1998 | Maahs |
| 5,853,420 | A | 12/1998 | Chevillon et al. |
| 5,871,537 | A * | 2/1999 | Holman et al. ............... 623/1.23 |
| 5,876,367 | A | 3/1999 | Kaganov et al. |
| 5,882,329 | A | 3/1999 | Patterson et al. |
| 5,893,869 | A | 4/1999 | Barnhart et al. |
| 5,895,391 | A | 4/1999 | Farnholtz |
| 5,895,399 | A | 4/1999 | Barbut et al. |
| 5,895,410 | A | 4/1999 | Forber et al. |
| 5,908,435 | A | 6/1999 | Samuels |
| 5,910,154 | A | 6/1999 | Tsugita et al. |
| 5,911,702 | A | 6/1999 | Romley et al. |
| 5,911,704 | A | 6/1999 | Humes |
| 5,911,717 | A | 6/1999 | Jacobsen et al. |
| 5,911,734 | A | 6/1999 | Tsugita et al. |
| 5,919,224 | A | 7/1999 | Thompson et al. |
| 5,925,062 | A | 7/1999 | Purdy |
| 5,925,063 | A | 7/1999 | Khosravi |
| 5,928,260 | A | 7/1999 | Chine et al. |
| 5,928,261 | A | 7/1999 | Ruiz |
| 5,938,683 | A | 8/1999 | Lefebvre |
| 5,941,896 | A | 8/1999 | Kerr |
| 5,944,728 | A | 8/1999 | Bates |
| 5,947,985 | A | 9/1999 | Imran |
| 5,947,995 | A * | 9/1999 | Samuels ....................... 606/200 |
| 5,948,017 | A | 9/1999 | Taheri |
| 5,951,567 | A | 9/1999 | Javier, Jr. et al. |
| 5,954,741 | A | 9/1999 | Fox |
| 5,954,742 | A | 9/1999 | Osypka |
| 5,954,745 | A | 9/1999 | Gertler et al. |
| 5,968,057 | A | 10/1999 | Taheri |
| 5,968,071 | A | 10/1999 | Chevillon et al. |
| 5,972,019 | A | 10/1999 | Engelson et al. |
| 5,976,162 | A | 11/1999 | Doan et al. |
| 5,976,172 | A | 11/1999 | Homsma et al. |
| 5,980,555 | A | 11/1999 | Barbut et al. |
| 5,984,947 | A | 11/1999 | Smith |
| 5,984,965 | A | 11/1999 | Knapp et al. |
| 5,989,281 | A | 11/1999 | Barbut et al. |
| 6,001,118 | A | 12/1999 | Daniel et al. |
| 6,007,557 | A | 12/1999 | Ambrisco et al. |
| 6,007,558 | A | 12/1999 | Ravenscloth et al. |
| 6,010,522 | A | 1/2000 | Barbut et al. |
| 6,013,093 | A | 1/2000 | Nott et al. |
| 6,015,424 | A | 1/2000 | Rosenbluth et al. |
| 6,027,520 | A | 2/2000 | Tsugita et al. |
| 6,036,717 | A | 3/2000 | Mers Kelly et al. |
| 6,036,720 | A | 3/2000 | Abrams et al. |
| 6,042,598 | A | 3/2000 | Tsugita et al. |
| 6,051,014 | A | 4/2000 | Jang |
| 6,051,015 | A | 4/2000 | Maahs |

(56) References Cited

U.S. PATENT DOCUMENTS

| | | | |
|---|---|---|---|
| 6,053,932 A | 4/2000 | Daniel et al. |
| 6,059,745 A | 5/2000 | Gelbfish |
| 6,059,813 A | 5/2000 | Vrba et al. |
| 6,059,814 A | 5/2000 | Ladd |
| 6,063,113 A | 5/2000 | Kavteladze et al. |
| 6,066,158 A | 5/2000 | Engelson et al. |
| 6,067,991 A * | 5/2000 | Forsell | 128/899 |
| 6,068,645 A | 5/2000 | Tu |
| 6,074,357 A | 6/2000 | Kaganov et al. |
| 6,077,274 A | 6/2000 | Ouchi et al. |
| 6,080,178 A | 6/2000 | Meglin |
| 6,083,239 A | 7/2000 | Addis |
| 6,086,577 A | 7/2000 | Ken et al. |
| 6,086,605 A | 7/2000 | Barbut et al. |
| 6,093,199 A | 7/2000 | Brown et al. |
| 6,096,053 A | 8/2000 | Bates |
| 6,096,070 A | 8/2000 | Ragheb et al. |
| 6,099,549 A | 8/2000 | Bosma et al. |
| 6,106,497 A | 8/2000 | Wang |
| 6,126,672 A | 10/2000 | Berryman et al. |
| 6,126,673 A | 10/2000 | Kim et al. |
| 6,129,739 A | 10/2000 | Khosravi |
| 6,136,016 A | 10/2000 | Barbut et al. |
| 6,146,396 A | 11/2000 | Konya et al. |
| 6,146,404 A | 11/2000 | Kim et al. |
| 6,152,931 A | 11/2000 | Nadal et al. |
| 6,152,946 A | 11/2000 | Broome et al. |
| 6,152,947 A | 11/2000 | Ambrisco et al. |
| 6,156,061 A | 12/2000 | Wallace et al. |
| 6,156,062 A | 12/2000 | McGuinness |
| 6,159,230 A | 12/2000 | Samuels |
| 6,165,179 A | 12/2000 | Cathcart et al. |
| 6,165,198 A | 12/2000 | McGurk et al. |
| 6,165,199 A | 12/2000 | Barbut |
| 6,165,200 A | 12/2000 | Tsugita et al. |
| 6,168,579 B1 | 1/2001 | Tsugita et al. |
| 6,168,603 B1 | 1/2001 | Leslie et al. |
| 6,168,610 B1 | 1/2001 | Marin et al. |
| 6,168,622 B1 | 1/2001 | Mazzocchi |
| 6,171,327 B1 | 1/2001 | Daniel et al. |
| 6,171,328 B1 | 1/2001 | Addis |
| 6,174,318 B1 | 1/2001 | Bates et al. |
| 6,179,851 B1 | 1/2001 | Barbut et al. |
| 6,179,859 B1 | 1/2001 | Bates et al. |
| 6,179,860 B1 | 1/2001 | Fulton, III et al. |
| 6,179,861 B1 * | 1/2001 | Khosravi et al. | 606/200 |
| 6,187,025 B1 | 2/2001 | Machek |
| 6,193,739 B1 | 2/2001 | Chevillon et al. |
| 6,203,561 B1 | 3/2001 | Ramee et al. |
| 6,206,931 B1 | 3/2001 | Cook et al. |
| 6,214,025 B1 | 4/2001 | Thistle et al. |
| 6,214,026 B1 | 4/2001 | Lepak et al. |
| 6,221,091 B1 | 4/2001 | Khosravi |
| 6,224,620 B1 | 5/2001 | Maahs |
| 6,231,588 B1 | 5/2001 | Zadno-Azizi |
| 6,231,589 B1 | 5/2001 | Wessman et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 * | 6/2001 | Lowery | 606/200 |
| 6,245,089 B1 | 6/2001 | Daniel et al. |
| 6,251,092 B1 | 6/2001 | Qin et al. |
| 6,251,122 B1 | 6/2001 | Tsukernik |
| 6,254,550 B1 | 7/2001 | McNamara et al. |
| 6,254,633 B1 | 7/2001 | Pinchuk et al. |
| 6,258,026 B1 | 7/2001 | Ravenscroft et al. |
| 6,258,115 B1 | 7/2001 | Dubrul |
| 6,258,120 B1 | 7/2001 | McKenzie et al. |
| 6,261,305 B1 | 7/2001 | Marotta et al. |
| 6,264,672 B1 | 7/2001 | Fisher |
| 6,267,776 B1 | 7/2001 | O'Connell |
| 6,267,777 B1 | 7/2001 | Bosma et al. |
| 6,273,900 B1 | 8/2001 | Nott et al. |
| 6,273,901 B1 | 8/2001 | Whitcher et al. |
| 6,277,125 B1 | 8/2001 | Barry et al. |
| 6,277,126 B1 | 8/2001 | Barry et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,710 B1 | 9/2001 | Cryer et al. |
| 6,299,604 B1 | 10/2001 | Ragheb et al. |
| 6,306,163 B1 | 10/2001 | Fitz |
| 6,309,399 B1 | 10/2001 | Barbut et al. |
| 6,312,444 B1 | 11/2001 | Barbut |
| 6,319,268 B1 | 11/2001 | Ambrisco et al. |
| 6,325,815 B1 | 12/2001 | Kusleika et al. |
| 6,325,816 B1 | 12/2001 | Fulton, III et al. |
| 6,328,755 B1 | 12/2001 | Marshall |
| 6,331,183 B1 | 12/2001 | Suon |
| 6,331,184 B1 | 12/2001 | Abrams |
| 6,334,864 B1 | 1/2002 | Amplatz et al. |
| 6,336,934 B1 | 1/2002 | Gilson et al. |
| 6,338,739 B1 | 1/2002 | Datta et al. |
| 6,340,364 B2 | 1/2002 | Kanesaka |
| 6,342,062 B1 | 1/2002 | Suon et al. |
| 6,342,063 B1 | 1/2002 | DeVries et al. |
| 6,344,048 B1 | 2/2002 | Chin et al. |
| 6,344,049 B1 | 2/2002 | Levinson et al. |
| 6,346,116 B1 | 2/2002 | Brooks et al. |
| 6,348,041 B1 | 2/2002 | Klint |
| 6,348,063 B1 | 2/2002 | Yassour et al. |
| 6,350,271 B1 | 2/2002 | Kurz et al. |
| 6,355,051 B1 | 3/2002 | Sisskind et al. |
| 6,358,228 B1 | 3/2002 | Tubman et al. |
| 6,361,545 B1 | 3/2002 | Macoviak et al. |
| 6,361,546 B1 | 3/2002 | Khosravi |
| 6,361,547 B1 | 3/2002 | Hieshima |
| 6,364,895 B1 | 4/2002 | Greenhalgh |
| 6,364,896 B1 | 4/2002 | Addis |
| 6,368,338 B1 | 4/2002 | Konya et al. |
| 6,371,961 B1 | 4/2002 | Osborne et al. |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,379,374 B1 | 4/2002 | Hieshima et al. |
| 6,380,457 B1 | 4/2002 | Yurek et al. |
| 6,383,146 B1 | 5/2002 | Klint |
| 6,383,171 B1 | 5/2002 | Gifford et al. |
| 6,383,174 B1 | 5/2002 | Eder |
| 6,383,193 B1 | 5/2002 | Cathcart et al. |
| 6,383,196 B1 | 5/2002 | Leslie et al. |
| 6,383,205 B1 | 5/2002 | Samson et al. |
| 6,383,206 B1 | 5/2002 | Gillick et al. |
| 6,391,044 B1 | 5/2002 | Yadav et al. |
| 6,391,045 B1 | 5/2002 | Kim et al. |
| 6,391,052 B2 | 5/2002 | Buirge et al. |
| 6,395,014 B1 | 5/2002 | Macoviak et al. |
| 6,402,771 B1 | 6/2002 | Palmer et al. |
| 6,402,772 B1 | 6/2002 | Amplatz et al. |
| 6,409,742 B1 | 6/2002 | Fulton, III et al. |
| 6,413,235 B1 | 7/2002 | Parodi |
| 6,416,530 B2 | 7/2002 | DeVries et al. |
| 6,419,686 B1 | 7/2002 | McLeod et al. |
| 6,423,052 B1 | 7/2002 | Escano |
| 6,423,086 B1 | 7/2002 | Barbut et al. |
| 6,425,909 B1 | 7/2002 | Dieck et al. |
| 6,428,557 B1 | 8/2002 | Hilaire |
| 6,428,558 B1 | 8/2002 | Jones et al. |
| 6,428,559 B1 | 8/2002 | Johnson |
| 6,432,122 B1 | 8/2002 | Gilson et al. |
| 6,436,112 B2 | 8/2002 | Wensel et al. |
| 6,436,120 B1 | 8/2002 | Meglin |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma et al. |
| 6,443,979 B1 | 9/2002 | Stalker et al. |
| 6,447,530 B1 | 9/2002 | Ostrovsky et al. |
| 6,447,531 B1 | 9/2002 | Amplatz |

(56) References Cited

U.S. PATENT DOCUMENTS

| | | | |
|---|---|---|---|
| 6,454,775 | B1 | 9/2002 | Demarais et al. |
| 6,458,139 | B1 | 10/2002 | Palmer et al. |
| 6,458,145 | B1 | 10/2002 | Ravenscroft et al. |
| 6,461,370 | B1 | 10/2002 | Gray et al. |
| 6,468,290 | B1 | 10/2002 | Weldon et al. |
| 6,468,291 | B2 | 10/2002 | Bates et al. |
| 6,482,222 | B1 | 11/2002 | Bruckheimer et al. |
| 6,485,456 | B1 | 11/2002 | Kletschka |
| 6,485,500 | B1 | 11/2002 | Kokish et al. |
| 6,485,501 | B1 | 11/2002 | Green |
| 6,485,502 | B2 | 11/2002 | Don Michael et al. |
| 6,491,712 | B1 | 12/2002 | O'Connor |
| 6,494,895 | B2 | 12/2002 | Addis |
| 6,497,709 | B1 | 12/2002 | Heath |
| 6,499,487 | B1 | 12/2002 | McKenzie et al. |
| 6,500,166 | B1 | 12/2002 | Zadno Azizi et al. |
| 6,500,191 | B2 | 12/2002 | Addis |
| 6,502,606 | B2 | 1/2003 | Klint |
| 6,506,203 | B1 | 1/2003 | Boyle et al. |
| 6,506,205 | B2 | 1/2003 | Goldberg et al. |
| 6,508,826 | B2 | 1/2003 | Murphy et al. |
| 6,511,492 | B1 | 1/2003 | Rosenbluth et al. |
| 6,511,496 | B1 | 1/2003 | Huter et al. |
| 6,511,497 | B1 | 1/2003 | Braun et al. |
| 6,511,503 | B1 | 1/2003 | Burkett et al. |
| 6,514,273 | B1 | 2/2003 | Voss et al. |
| 6,517,559 | B1 | 2/2003 | O'Connell |
| 6,520,978 | B1 | 2/2003 | Blackledge et al. |
| 6,520,983 | B1 | 2/2003 | Colgan et al. |
| 6,527,746 | B1 | 3/2003 | Oslund et al. |
| 6,527,791 | B2 | 3/2003 | Fisher |
| 6,527,962 | B1 | 3/2003 | Nadal |
| 6,530,935 | B2 | 3/2003 | Wensel et al. |
| 6,530,939 | B1 | 3/2003 | Hopkins et al. |
| 6,530,940 | B2 | 3/2003 | Fisher |
| 6,533,770 | B1 | 3/2003 | Lepulu et al. |
| 6,533,800 | B1 | 3/2003 | Barbut |
| 6,537,293 | B1 | 3/2003 | Berryman et al. |
| 6,537,294 | B1 | 3/2003 | Boyle et al. |
| 6,537,296 | B2 | 3/2003 | Levinson et al. |
| 6,537,297 | B2 | 3/2003 | Tsugita et al. |
| 6,540,722 | B1 | 4/2003 | Boyle et al. |
| 6,540,767 | B1 | 4/2003 | Walak et al. |
| 6,540,768 | B1 | 4/2003 | Diaz et al. |
| 6,544,221 | B1 | 4/2003 | Kokish et al. |
| 6,544,276 | B1 | 4/2003 | Azizi |
| 6,544,278 | B1 | 4/2003 | Vrba et al. |
| 6,544,279 | B1 | 4/2003 | Hopkins et al. |
| 6,544,280 | B1 | 4/2003 | Daniel et al. |
| 6,547,759 | B1 | 4/2003 | Fisher |
| 6,551,303 | B1 | 4/2003 | Van Tassel et al. |
| 6,551,341 | B2 | 4/2003 | Boylan et al. |
| 6,551,342 | B1 | 4/2003 | Shen et al. |
| 6,554,849 | B1 | 4/2003 | Jones et al. |
| 6,558,404 | B2 | 5/2003 | Tsukernik |
| 6,558,405 | B1 | 5/2003 | McInnes |
| 6,558,406 | B2 | 5/2003 | Okada |
| 6,562,058 | B2 | 5/2003 | Seguin et al. |
| 6,565,591 | B2 | 5/2003 | Brady et al. |
| 6,569,147 | B1 | 5/2003 | Evans et al. |
| 6,569,183 | B1 | 5/2003 | Kim et al. |
| 6,569,184 | B2 | 5/2003 | Huter |
| 6,575,995 | B1 | 6/2003 | Huter et al. |
| 6,575,996 | B1 | 6/2003 | Denison et al. |
| 6,575,997 | B1 | 6/2003 | Palmer et al. |
| 6,579,303 | B2 | 6/2003 | Amplatz |
| 6,582,396 | B1 | 6/2003 | Parodi |
| 6,582,447 | B1 | 6/2003 | Patel et al. |
| 6,582,448 | B1 | 6/2003 | Boyle et al. |
| 6,589,227 | B2 | 7/2003 | Klint |
| 6,589,230 | B2 | 7/2003 | Gia et al. |
| 6,589,263 | B1 | 7/2003 | Hopkins et al. |
| 6,589,264 | B1 | 7/2003 | Barbut et al. |
| 6,589,265 | B1 | 7/2003 | Palmer et al. |
| 6,589,266 | B2 | 7/2003 | Whitcher et al. |
| 6,592,546 | B1 | 7/2003 | Barbut et al. |
| 6,592,606 | B2 | 7/2003 | Huter et al. |
| 6,592,616 | B1 | 7/2003 | Stack et al. |
| 6,595,983 | B2 | 7/2003 | Voda |
| 6,596,011 | B2 | 7/2003 | Johnson et al. |
| 6,599,275 | B1 | 7/2003 | Fischer, Jr. |
| 6,599,307 | B1 | 7/2003 | Huter et al. |
| 6,599,308 | B2 | 7/2003 | Amplatz |
| 6,602,271 | B2 | 8/2003 | Adams et al. |
| 6,602,273 | B2 | 8/2003 | Marshall |
| 6,602,280 | B2 | 8/2003 | Chobotov |
| 6,605,102 | B1 | 8/2003 | Mazzocchi et al. |
| 6,607,506 | B2 | 8/2003 | Kletschka |
| 6,610,077 | B1 | 8/2003 | Hancock et al. |
| 6,611,720 | B2 | 8/2003 | Hata et al. |
| 6,613,074 | B1 | 9/2003 | Mitelberg et al. |
| 6,616,679 | B1 | 9/2003 | Khosravi et al. |
| 6,616,680 | B1 | 9/2003 | Thielen |
| 6,616,681 | B2 | 9/2003 | Hanson et al. |
| 6,616,682 | B2 | 9/2003 | Joergensen et al. |
| 6,620,148 | B1 | 9/2003 | Tsugita |
| 6,620,182 | B1 | 9/2003 | Khosravi et al. |
| 6,623,450 | B1 | 9/2003 | Dutta |
| 6,623,506 | B2 | 9/2003 | McGuckin, Jr. et al. |
| 6,629,953 | B1 | 10/2003 | Boyd |
| 6,635,068 | B1 | 10/2003 | Dubrul et al. |
| 6,635,069 | B1 | 10/2003 | Teoh et al. |
| 6,635,070 | B2 | 10/2003 | Leeflang et al. |
| 6,638,293 | B1 | 10/2003 | Makower et al. |
| 6,638,294 | B1 | 10/2003 | Palmer |
| 6,638,372 | B1 | 10/2003 | Abrams et al. |
| 6,641,590 | B1 | 11/2003 | Palmer et al. |
| 6,641,605 | B1 | 11/2003 | Stergiopulos |
| 6,645,160 | B1 | 11/2003 | Heesch |
| 6,645,220 | B1 | 11/2003 | Huter et al. |
| 6,645,221 | B1 | 11/2003 | Richter |
| 6,645,222 | B1 | 11/2003 | Parodi et al. |
| 6,645,223 | B2 | 11/2003 | Boyle et al. |
| 6,645,224 | B2 | 11/2003 | Gilson et al. |
| 6,652,554 | B1 | 11/2003 | Wholey et al. |
| 6,652,557 | B1 | 11/2003 | MacDonald |
| 6,652,558 | B2 | 11/2003 | Patel et al. |
| 6,656,201 | B2 | 12/2003 | Ferrera et al. |
| 6,656,202 | B2 | 12/2003 | Papp et al. |
| 6,656,203 | B2 | 12/2003 | Roth et al. |
| 6,656,204 | B2 | 12/2003 | Ambrisco et al. |
| 6,656,351 | B2 | 12/2003 | Boyle |
| 6,660,021 | B1 | 12/2003 | Palmer et al. |
| 6,663,613 | B1 | 12/2003 | Evans et al. |
| 6,663,650 | B2 | 12/2003 | Sepetka et al. |
| 6,663,651 | B2 | 12/2003 | Krolik et al. |
| 6,663,652 | B2 | 12/2003 | Daniel et al. |
| 6,676,682 | B1 | 1/2004 | Tsugita et al. |
| 6,679,902 | B1 | 1/2004 | Boyle et al. |
| 6,689,144 | B2 | 2/2004 | Gerberding |
| 6,695,813 | B1 | 2/2004 | Boyle et al. |
| 6,695,865 | B2 | 2/2004 | Boyle et al. |
| 6,702,834 | B1 | 3/2004 | Boylan et al. |
| 6,709,450 | B2 | 3/2004 | Kang et al. |
| 6,712,835 | B2 | 3/2004 | Mazzocchi et al. |
| 6,716,207 | B2 | 4/2004 | Farnholtz |
| 6,716,231 | B1 | 4/2004 | Rafiee et al. |
| 6,726,701 | B2 | 4/2004 | Gilson et al. |
| 6,730,064 | B2 | 5/2004 | Ragheb et al. |
| 6,755,855 | B2 | 6/2004 | Yurek et al. |
| 6,755,856 | B2 | 6/2004 | Fierens et al. |
| 6,758,855 | B2 | 7/2004 | Fulton, III et al. |
| 6,761,727 | B1 | 7/2004 | Ladd |
| 6,773,446 | B1 | 8/2004 | Dwyer et al. |
| 6,773,448 | B2 | 8/2004 | Kusleika et al. |
| 6,774,278 | B1 | 8/2004 | Ragheb et al. |
| 6,780,175 | B1 | 8/2004 | Sachdeva et al. |
| 6,793,667 | B2 | 9/2004 | Hebert et al. |
| 6,793,668 | B1 | 9/2004 | Fisher |
| 6,833,002 | B2 | 12/2004 | Stack et al. |
| 6,855,154 | B2 | 2/2005 | Abdel-Gawwad |
| 6,866,677 | B2 | 3/2005 | Douk et al. |
| 6,866,680 | B2 | 3/2005 | Yassour et al. |
| 6,872,211 | B2 | 3/2005 | White et al. |

(56) References Cited

U.S. PATENT DOCUMENTS

| | | | |
|---|---|---|---|
| 6,878,153 B2 | 4/2005 | Linder et al. |
| 6,896,691 B2 | 5/2005 | Boylan et al. |
| 6,929,709 B2 | 8/2005 | Smith |
| 6,932,831 B2 | 8/2005 | Forber |
| 6,936,059 B2 | 8/2005 | Belef |
| 6,939,361 B1 | 9/2005 | Kleshinski |
| 6,942,682 B2 | 9/2005 | Vrba et al. |
| 6,955,685 B2 | 10/2005 | Escamilla et al. |
| 6,964,670 B1 * | 11/2005 | Shah et al. ................ 606/200 |
| 6,964,674 B1 | 11/2005 | Matsuura et al. |
| 6,969,396 B2 | 11/2005 | Krolik et al. |
| 6,974,469 B2 | 12/2005 | Broome et al. |
| 6,974,473 B2 | 12/2005 | Barclay et al. |
| 6,986,784 B1 | 1/2006 | Weiser et al. |
| 6,991,641 B2 | 1/2006 | Diaz et al. |
| 7,128,073 B1 | 10/2006 | van der Burg et al. |
| 7,166,120 B2 | 1/2007 | Kusleika |
| 7,174,636 B2 | 2/2007 | Lowe |
| 7,189,249 B2 | 3/2007 | Hart et al. |
| 7,204,847 B1 | 4/2007 | Gambale |
| 7,220,271 B2 | 5/2007 | Clubb et al. |
| 7,255,687 B2 | 8/2007 | Huang et al. |
| 7,285,130 B2 | 10/2007 | Austin |
| 7,303,575 B2 | 12/2007 | Ogle |
| 7,306,619 B1 | 12/2007 | Palmer |
| 7,371,248 B2 | 5/2008 | Dapolito et al. |
| 7,393,358 B2 | 7/2008 | Malewicz |
| 7,604,649 B2 | 10/2009 | McGuckin et al. |
| 7,666,216 B2 | 2/2010 | Hogendijk et al. |
| 7,708,770 B2 | 5/2010 | Linder et al. |
| 7,731,722 B2 | 6/2010 | Lavelle et al. |
| 7,731,731 B2 | 6/2010 | Abela |
| 7,766,934 B2 | 8/2010 | Pal et al. |
| 2001/0000799 A1 | 5/2001 | Wessman et al. |
| 2001/0001817 A1 | 5/2001 | Humes |
| 2001/0005789 A1 | 6/2001 | Root et al. |
| 2001/0007947 A1 | 7/2001 | Kanesaka |
| 2001/0011181 A1 | 8/2001 | DiMatteo |
| 2001/0011182 A1 | 8/2001 | Dubrul et al. |
| 2001/0012951 A1 | 8/2001 | Bates et al. |
| 2001/0016755 A1 | 8/2001 | Addis |
| 2001/0020175 A1 | 9/2001 | Yassour et al. |
| 2001/0023358 A1 | 9/2001 | Tsukernik |
| 2001/0025187 A1 | 9/2001 | Okada |
| 2001/0031980 A1 | 10/2001 | Wensel et al. |
| 2001/0031981 A1 | 10/2001 | Evans et al. |
| 2001/0031982 A1 | 10/2001 | Peterson et al. |
| 2001/0039431 A1 | 11/2001 | DeVries et al. |
| 2001/0039432 A1 | 11/2001 | Whitcher et al. |
| 2001/0041908 A1 | 11/2001 | Levinson et al. |
| 2001/0041909 A1 | 11/2001 | Tsugita et al. |
| 2001/0041928 A1 | 11/2001 | Pavcnik et al. |
| 2001/0044632 A1 | 11/2001 | Daniel et al. |
| 2001/0044634 A1 | 11/2001 | Don Michael et al. |
| 2001/0053921 A1 | 12/2001 | Jang |
| 2002/0002383 A1 * | 1/2002 | Sepetka et al. ................ 606/200 |
| 2002/0002384 A1 | 1/2002 | Gilson et al. |
| 2002/0004667 A1 | 1/2002 | Adams et al. |
| 2002/0016564 A1 | 2/2002 | Courtney et al. |
| 2002/0016609 A1 | 2/2002 | Wensel et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0026212 A1 | 2/2002 | Wholey et al. |
| 2002/0026213 A1 | 2/2002 | Gilson et al. |
| 2002/0032460 A1 | 3/2002 | Kusleika et al. |
| 2002/0032461 A1 | 3/2002 | Marshall |
| 2002/0042626 A1 | 4/2002 | Hanson et al. |
| 2002/0042627 A1 | 4/2002 | Brady et al. |
| 2002/0045915 A1 | 4/2002 | Balceta et al. |
| 2002/0045916 A1 | 4/2002 | Gray et al. |
| 2002/0045918 A1 | 4/2002 | Suon et al. |
| 2002/0049452 A1 | 4/2002 | Kurz et al. |
| 2002/0049468 A1 | 4/2002 | Streeter et al. |
| 2002/0052627 A1 | 5/2002 | Boylan et al. |
| 2002/0058904 A1 | 5/2002 | Boock et al. |
| 2002/0058911 A1 | 5/2002 | Gilson et al. |
| 2002/0058963 A1 | 5/2002 | Vale et al. |
| 2002/0058964 A1 | 5/2002 | Addis |
| 2002/0062133 A1 | 5/2002 | Gilson et al. |
| 2002/0062134 A1 * | 5/2002 | Barbut et al. ................ 606/200 |
| 2002/0062135 A1 | 5/2002 | Mazzocchi et al. |
| 2002/0065507 A1 | 5/2002 | Zadno-Azizi |
| 2002/0068954 A1 | 6/2002 | Foster |
| 2002/0068955 A1 | 6/2002 | Khosravi |
| 2002/0072764 A1 | 6/2002 | Sepetka et al. |
| 2002/0072765 A1 | 6/2002 | Mazzocchi et al. |
| 2002/0077596 A1 | 6/2002 | McKenzie et al. |
| 2002/0082558 A1 | 6/2002 | Samson et al. |
| 2002/0082639 A1 | 6/2002 | Broome et al. |
| 2002/0087187 A1 | 7/2002 | Mazzocchi et al. |
| 2002/0090389 A1 | 7/2002 | Humes et al. |
| 2002/0091407 A1 | 7/2002 | Zadno-Azizi et al. |
| 2002/0091408 A1 | 7/2002 | Sutton et al. |
| 2002/0091409 A1 | 7/2002 | Sutton et al. |
| 2002/0095170 A1 | 7/2002 | Krolik et al. |
| 2002/0095171 A1 | 7/2002 | Belef |
| 2002/0095172 A1 | 7/2002 | Mazzocchi et al. |
| 2002/0095173 A1 | 7/2002 | Mazzocchi et al. |
| 2002/0095174 A1 | 7/2002 | Tsugita et al. |
| 2002/0099405 A1 | 7/2002 | Yurek et al. |
| 2002/0099407 A1 | 7/2002 | Becker et al. |
| 2002/0099435 A1 | 7/2002 | Stinson |
| 2002/0103501 A1 | 8/2002 | Diaz et al. |
| 2002/0107541 A1 | 8/2002 | Vale et al. |
| 2002/0111647 A1 | 8/2002 | Khairkhahan et al. |
| 2002/0111648 A1 | 8/2002 | Kusleika et al. |
| 2002/0111649 A1 | 8/2002 | Russo et al. |
| 2002/0116024 A1 | 8/2002 | Goldberg et al. |
| 2002/0120226 A1 | 8/2002 | Beck |
| 2002/0120286 A1 | 8/2002 | DoBrava et al. |
| 2002/0120287 A1 | 8/2002 | Huter |
| 2002/0123720 A1 | 9/2002 | Kusleika et al. |
| 2002/0123755 A1 | 9/2002 | Lowe et al. |
| 2002/0123759 A1 | 9/2002 | Amplatz |
| 2002/0123766 A1 | 9/2002 | Seguin et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133191 A1 | 9/2002 | Khosravi et al. |
| 2002/0133192 A1 | 9/2002 | Kusleika et al. |
| 2002/0138094 A1 | 9/2002 | Borillo et al. |
| 2002/0138095 A1 | 9/2002 | Mazzocchi et al. |
| 2002/0138096 A1 | 9/2002 | Hieshima |
| 2002/0138097 A1 | 9/2002 | Ostrovsky et al. |
| 2002/0143360 A1 | 10/2002 | Douk et al. |
| 2002/0143361 A1 | 10/2002 | Douk et al. |
| 2002/0143362 A1 | 10/2002 | Macoviak et al. |
| 2002/0151927 A1 | 10/2002 | Douk et al. |
| 2002/0151928 A1 | 10/2002 | Leslie et al. |
| 2002/0156520 A1 | 10/2002 | Boylan et al. |
| 2002/0161389 A1 | 10/2002 | Boyle et al. |
| 2002/0161390 A1 | 10/2002 | Mouw |
| 2002/0161391 A1 | 10/2002 | Murphy et al. |
| 2002/0161392 A1 | 10/2002 | Dubrul |
| 2002/0161393 A1 | 10/2002 | Demond et al. |
| 2002/0161394 A1 | 10/2002 | Macoviak et al. |
| 2002/0161395 A1 | 10/2002 | Douk et al. |
| 2002/0161396 A1 | 10/2002 | Jang et al. |
| 2002/0165557 A1 | 11/2002 | McAlister |
| 2002/0165573 A1 | 11/2002 | Barbut |
| 2002/0165576 A1 | 11/2002 | Boyle et al. |
| 2002/0165598 A1 | 11/2002 | Wahr et al. |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173819 A1 | 11/2002 | Leeflang et al. |
| 2002/0177872 A1 | 11/2002 | Papp et al. |
| 2002/0177899 A1 | 11/2002 | Eum et al. |
| 2002/0183781 A1 | 12/2002 | Casey et al. |
| 2002/0183782 A1 | 12/2002 | Tsugita et al. |
| 2002/0183783 A1 | 12/2002 | Shadduck |
| 2002/0188313 A1 | 12/2002 | Johnson et al. |
| 2002/0188314 A1 | 12/2002 | Anderson et al. |

(56) References Cited

U.S. PATENT DOCUMENTS

| | | |
|---|---|---|
| 2002/0193824 A1 | 12/2002 | Boylan et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2002/0198561 A1 | 12/2002 | Amplatz |
| 2003/0004536 A1 | 1/2003 | Boylan et al. |
| 2003/0004537 A1 | 1/2003 | Boyle et al. |
| 2003/0004538 A1 | 1/2003 | Secrest et al. |
| 2003/0004539 A1 | 1/2003 | Linder et al. |
| 2003/0004540 A1 | 1/2003 | Linder et al. |
| 2003/0004541 A1 | 1/2003 | Wensel et al. |
| 2003/0004542 A1 | 1/2003 | Wensel et al. |
| 2003/0009146 A1 | 1/2003 | Muni et al. |
| 2003/0009189 A1 | 1/2003 | Gilson et al. |
| 2003/0009190 A1 | 1/2003 | Kletschka et al. |
| 2003/0009191 A1 | 1/2003 | Wensel et al. |
| 2003/0014072 A1 | 1/2003 | Wensel et al. |
| 2003/0018354 A1 | 1/2003 | Roth et al. |
| 2003/0018355 A1 | 1/2003 | Goto et al. |
| 2003/0023263 A1 | 1/2003 | Krolik et al. |
| 2003/0023264 A1 | 1/2003 | Dieck et al. |
| 2003/0023265 A1 | 1/2003 | Forber |
| 2003/0032976 A1 | 2/2003 | Boucck |
| 2003/0032977 A1 | 2/2003 | Brady |
| 2003/0040772 A1 | 2/2003 | Hyodoh et al. |
| 2003/0045897 A1 | 3/2003 | Huter et al. |
| 2003/0045898 A1 | 3/2003 | Harrison et al. |
| 2003/0050662 A1 | 3/2003 | Don Michael |
| 2003/0055452 A1 | 3/2003 | Joergensen et al. |
| 2003/0055480 A1 | 3/2003 | Fischell et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0065355 A1 | 4/2003 | Weber |
| 2003/0065356 A1 | 4/2003 | Tsugita et al. |
| 2003/0069596 A1 | 4/2003 | Eskuri |
| 2003/0073979 A1 | 4/2003 | Naimark et al. |
| 2003/0074019 A1 | 4/2003 | Gray et al. |
| 2003/0074054 A1 | 4/2003 | Duerig et al. |
| 2003/0078614 A1 | 4/2003 | Salahieh et al. |
| 2003/0083608 A1 | 5/2003 | Evans et al. |
| 2003/0083692 A1 | 5/2003 | Vrba et al. |
| 2003/0083693 A1 | 5/2003 | Daniel et al. |
| 2003/0088211 A1 | 5/2003 | Anderson et al. |
| 2003/0088266 A1 | 5/2003 | Bowlin |
| 2003/0093110 A1 | 5/2003 | Vale |
| 2003/0093112 A1 | 5/2003 | Addis |
| 2003/0097094 A1 | 5/2003 | Ouriel et al. |
| 2003/0097145 A1 | 5/2003 | Goldberg et al. |
| 2003/0100917 A1 | 5/2003 | Boyle et al. |
| 2003/0100918 A1 | 5/2003 | Duane |
| 2003/0100919 A1 | 5/2003 | Hopkins et al. |
| 2003/0105472 A1 | 6/2003 | McAlister |
| 2003/0105484 A1 | 6/2003 | Boyle et al. |
| 2003/0105486 A1 | 6/2003 | Murphy et al. |
| 2003/0109824 A1 | 6/2003 | Anderson et al. |
| 2003/0109897 A1 | 6/2003 | Walak et al. |
| 2003/0109916 A1 | 6/2003 | Don Michael |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0120304 A1 | 6/2003 | Kaganov et al. |
| 2003/0125764 A1 | 7/2003 | Brady et al. |
| 2003/0125765 A1 | 7/2003 | Blackledge et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135232 A1 | 7/2003 | Douk et al. |
| 2003/0135233 A1 | 7/2003 | Bates et al. |
| 2003/0139764 A1 | 7/2003 | Levinson et al. |
| 2003/0139765 A1 | 7/2003 | Patel et al. |
| 2003/0144685 A1 | 7/2003 | Boyle et al. |
| 2003/0144686 A1 | 7/2003 | Martinez et al. |
| 2003/0144687 A1 | 7/2003 | Brady et al. |
| 2003/0144688 A1 | 7/2003 | Brady et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0153944 A1 | 8/2003 | Phung et al. |
| 2003/0153945 A1 | 8/2003 | Patel et al. |
| 2003/0158518 A1 | 8/2003 | Schonholz et al. |
| 2003/0158574 A1 | 8/2003 | Esch et al. |
| 2003/0158575 A1 | 8/2003 | Boylan et al. |
| 2003/0163158 A1 | 8/2003 | White |
| 2003/0163159 A1 | 8/2003 | Patel et al. |
| 2003/0167068 A1 | 9/2003 | Amplatz |
| 2003/0167069 A1 | 9/2003 | Gonzales et al. |
| 2003/0171769 A1 | 9/2003 | Barbut |
| 2003/0171770 A1* | 9/2003 | Kusleika et al. ............... 606/200 |
| 2003/0171771 A1 | 9/2003 | Anderson et al. |
| 2003/0171772 A1 | 9/2003 | Amplatz |
| 2003/0171800 A1 | 9/2003 | Bicek et al. |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176887 A1 | 9/2003 | Petersen |
| 2003/0176888 A1 | 9/2003 | O'Connell |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191492 A1 | 10/2003 | Gellman et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199917 A1 | 10/2003 | Knudson et al. |
| 2003/0199918 A1 | 10/2003 | Patel et al. |
| 2003/0199919 A1 | 10/2003 | Palmer et al. |
| 2003/0199920 A1 | 10/2003 | Boylan et al. |
| 2003/0199921 A1 | 10/2003 | Palmer et al. |
| 2003/0204168 A1 | 10/2003 | Bosma et al. |
| 2003/0204202 A1 | 10/2003 | Palmer et al. |
| 2003/0204203 A1 | 10/2003 | Khairkhahan et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0208253 A1 | 11/2003 | Beyer et al. |
| 2003/0212428 A1 | 11/2003 | Richter |
| 2003/0212429 A1 | 11/2003 | Keegan et al. |
| 2003/0212431 A1 | 11/2003 | Brady et al. |
| 2003/0212432 A1 | 11/2003 | Khairkhahan et al. |
| 2003/0212433 A1 | 11/2003 | Ambrisco et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0220667 A1 | 11/2003 | Van der Burg et al. |
| 2003/0225418 A1 | 12/2003 | Esksuri et al. |
| 2003/0225435 A1 | 12/2003 | Huter et al. |
| 2003/0229374 A1 | 12/2003 | Brady et al. |
| 2003/0233117 A1 | 12/2003 | Adams et al. |
| 2004/0006364 A1 | 1/2004 | Ladd |
| 2004/0006365 A1 | 1/2004 | Brady et al. |
| 2004/0006370 A1 | 1/2004 | Tsugita |
| 2004/0015152 A1 | 1/2004 | Day |
| 2004/0039412 A1 | 2/2004 | Isshiki et al. |
| 2004/0049226 A1 | 3/2004 | Keegan et al. |
| 2004/0054394 A1 | 3/2004 | Lee |

(56) References Cited

U.S. PATENT DOCUMENTS

| | | |
|---|---|---|
| 2004/0054395 A1 | 3/2004 | Lee et al. |
| 2004/0059372 A1 | 3/2004 | Tsugita |
| 2004/0064067 A1 | 4/2004 | Ward |
| 2004/0064179 A1 | 4/2004 | Linder et al. |
| 2004/0068271 A1 | 4/2004 | McAlister |
| 2004/0078044 A1 | 4/2004 | Kear |
| 2004/0082962 A1 | 4/2004 | Demarais et al. |
| 2004/0088038 A1 | 5/2004 | Dehnad et al. |
| 2004/0093009 A1 | 5/2004 | Denison et al. |
| 2004/0093012 A1 | 5/2004 | Cully et al. |
| 2004/0093016 A1 | 5/2004 | Root et al. |
| 2004/0093059 A1 | 5/2004 | Lee et al. |
| 2004/0098022 A1 | 5/2004 | Barone |
| 2004/0098026 A1 | 5/2004 | Joergensen et al. |
| 2004/0098033 A1 | 5/2004 | Leeflang et al. |
| 2004/0098112 A1 | 5/2004 | DiMatteo et al. |
| 2004/0102719 A1 | 5/2004 | Keith et al. |
| 2004/0106944 A1 | 6/2004 | Daniel et al. |
| 2004/0116831 A1 | 6/2004 | Vrba |
| 2004/0133232 A1 | 7/2004 | Rosenbluth et al. |
| 2004/0138696 A1 | 7/2004 | Drasler et al. |
| 2004/0153118 A1 | 8/2004 | Clubb et al. |
| 2004/0158278 A1 | 8/2004 | Becker et al. |
| 2004/0162576 A1* | 8/2004 | Barbut et al. ............. 606/200 |
| 2004/0164030 A1 | 8/2004 | Lowe et al. |
| 2004/0167567 A1 | 8/2004 | Cano et al. |
| 2004/0176794 A1 | 9/2004 | Khosravi |
| 2004/0176833 A1 | 9/2004 | Pavcnik et al. |
| 2004/0199201 A1 | 10/2004 | Kellett et al. |
| 2004/0199203 A1 | 10/2004 | Oslund et al. |
| 2004/0204737 A1* | 10/2004 | Boismier et al. ........... 606/200 |
| 2004/0215322 A1 | 10/2004 | Kerr |
| 2004/0225321 A1 | 11/2004 | Krolik et al. |
| 2004/0236369 A1 | 11/2004 | Dubrul |
| 2005/0004663 A1 | 1/2005 | Llanos et al. |
| 2005/0021125 A1 | 1/2005 | Stack et al. |
| 2005/0027345 A1 | 2/2005 | Horan et al. |
| 2005/0038468 A1 | 2/2005 | Panetta et al. |
| 2005/0038503 A1 | 2/2005 | Greenhaigh |
| 2005/0043743 A1 | 2/2005 | Dennis |
| 2005/0043756 A1 | 2/2005 | Lavelle et al. |
| 2005/0043780 A1 | 2/2005 | Gifford et al. |
| 2005/0049668 A1 | 3/2005 | Jones et al. |
| 2005/0126979 A1* | 6/2005 | Lowe et al. ............. 210/321.67 |
| 2005/0137696 A1 | 6/2005 | Salahieh et al. |
| 2005/0149110 A1 | 7/2005 | Wholey et al. |
| 2005/0165480 A1 | 7/2005 | Jordan et al. |
| 2005/0177186 A1 | 8/2005 | Cully et al. |
| 2005/0177246 A1 | 8/2005 | Datta et al. |
| 2005/0197688 A1 | 9/2005 | Theron et al. |
| 2005/0209634 A1 | 9/2005 | Brady et al. |
| 2005/0216053 A1 | 9/2005 | Douk et al. |
| 2005/0217767 A1 | 10/2005 | Barvosa-Carter et al. |
| 2005/0228474 A1 | 10/2005 | Laguna |
| 2006/0009790 A1 | 1/2006 | Kleshinski et al. |
| 2006/0009798 A1 | 1/2006 | Callister et al. |
| 2006/0020334 A1 | 1/2006 | Lashinski et al. |
| 2006/0025804 A1 | 2/2006 | Krolik et al. |
| 2006/0030923 A1 | 2/2006 | Gunderson |
| 2006/0074474 A1 | 4/2006 | Theron |
| 2006/0100544 A1 | 5/2006 | Ayala et al. |
| 2006/0100545 A1 | 5/2006 | Ayala et al. |
| 2006/0142845 A1 | 6/2006 | Molaei et al. |
| 2006/0161186 A1* | 7/2006 | Hassler et al. ............. 606/153 |
| 2006/0161241 A1 | 7/2006 | Barbut et al. |
| 2006/0184194 A1 | 8/2006 | Pal et al. |
| 2006/0200221 A1 | 9/2006 | Malewicz |
| 2006/0229660 A1 | 10/2006 | Pal et al. |
| 2006/0264707 A1 | 11/2006 | Kinney |
| 2006/0287667 A1 | 12/2006 | Abela |
| 2006/0287668 A1 | 12/2006 | Fawzi et al. |
| 2007/0038241 A1 | 2/2007 | Pal |
| 2007/0066991 A1 | 3/2007 | Magnuson |
| 2007/0100372 A1 | 5/2007 | Schaeffer |
| 2007/0112374 A1 | 5/2007 | Paul, Jr. et al. |
| 2007/0129752 A1 | 6/2007 | Webler et al. |
| 2007/0149996 A1 | 6/2007 | Coughlin |
| 2007/0167974 A1 | 7/2007 | Cully et al. |
| 2007/0185521 A1 | 8/2007 | Bui et al. |
| 2007/0250108 A1 | 10/2007 | Boyle et al. |
| 2007/0288054 A1 | 12/2007 | Tanaka et al. |
| 2008/0015518 A1 | 1/2008 | Huang et al. |
| 2008/0027481 A1 | 1/2008 | Gilson et al. |
| 2008/0103522 A1 | 5/2008 | Steingisser et al. |
| 2008/0154236 A1 | 6/2008 | Elkins et al. |
| 2008/0167629 A1 | 7/2008 | Dann et al. |
| 2008/0255587 A1 | 10/2008 | Cully et al. |
| 2008/0255606 A1 | 10/2008 | Mitra et al. |
| 2008/0262337 A1 | 10/2008 | Falwell et al. |
| 2008/0275569 A1 | 11/2008 | Lesh |

FOREIGN PATENT DOCUMENTS

| | | | |
|---|---|---|---|
| EP | 1310219 A2 | | 5/2003 |
| EP | 1516601 | | 3/2005 |
| EP | 1557137 A1 | | 7/2005 |
| WO | WO 92/03097 | * | 3/1992 |
| WO | WO 96/10591 | | 4/1996 |
| WO | WO 99/16382 | | 4/1999 |
| WO | WO 99/23976 | | 5/1999 |
| WO | WO 99/44510 | | 9/1999 |
| WO | WO 01/82831 | | 11/2001 |
| WO | WO 03/077799 A2 | | 9/2003 |
| WO | WO 2006/138391 A2 | | 12/2006 |

OTHER PUBLICATIONS

Rubicon Embolic Filter, The Next Generation of EM, Rubicon Medical, www.rubiconmed.com.
Heeschen et al., Nature Medicine 7 (2001), No. 7, pp. 833-839.
Johnson et al., Circulation Research 94 (2004), No. 2, pp. 262-268.
International Search Report and Written Opinion for PCT/US2007/020300.
Brochure, "Shuttle Select ™ System for Carotid Artery Access," (2004), pp. 1-3.
Brochure, "Slip-Cath® Angiographic Selective Catheters," (2004), pp. 1-6.
Finol, E.A. et al., "Performance Assessment of Embolic Protection Filters for Carotid Artery Stenting," *Modelling in Medicine and Biology IV*, (2005), vol. 8, pp. 133.

* cited by examiner

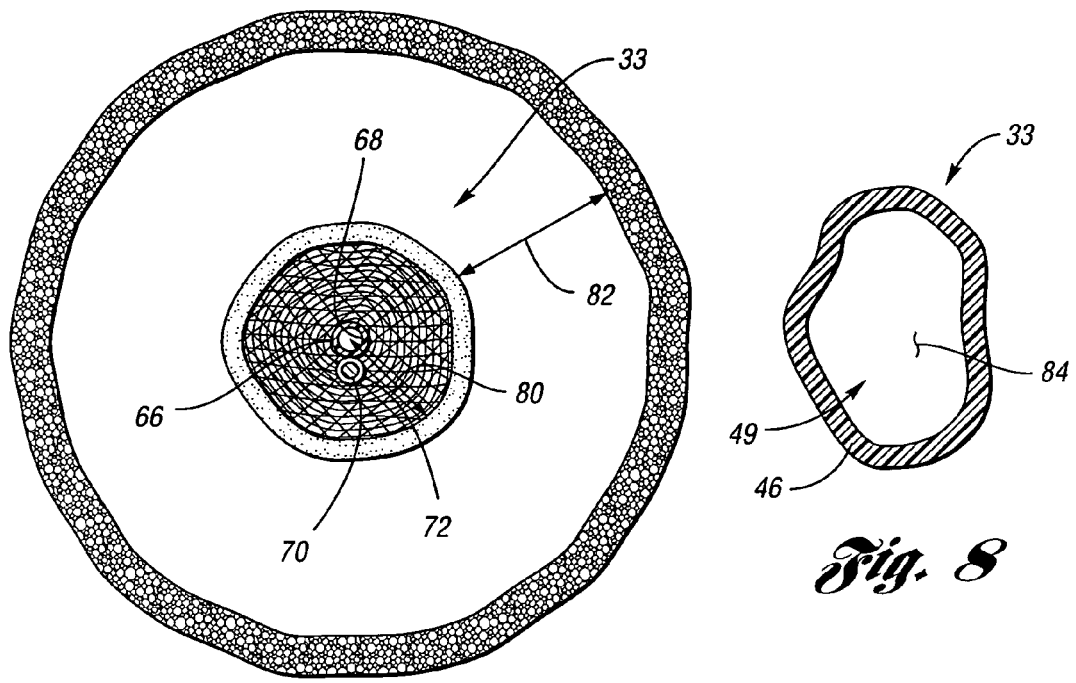
Fig. 7
Fig. 8
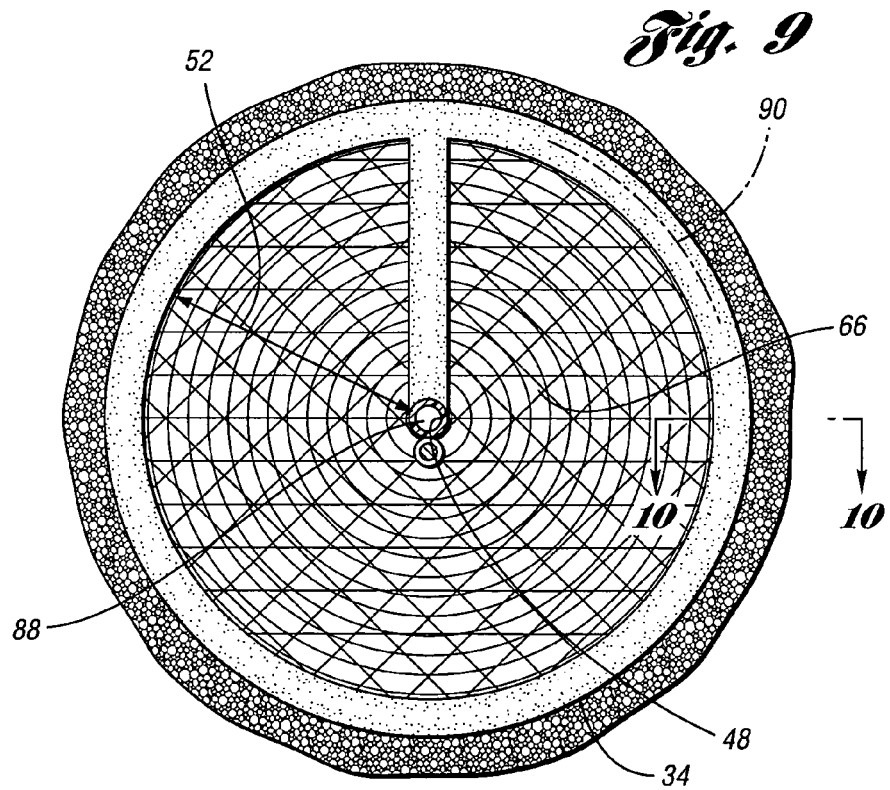
Fig. 9

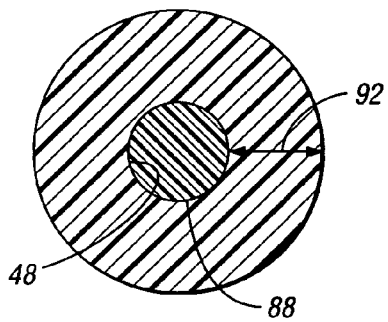
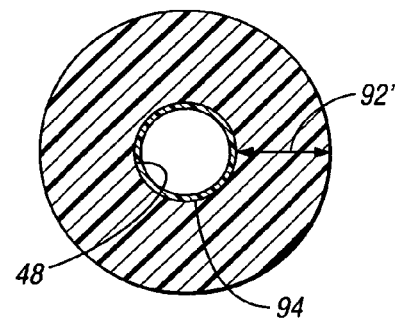
*Fig. 10*      *Fig. 11*
*Fig. 13*
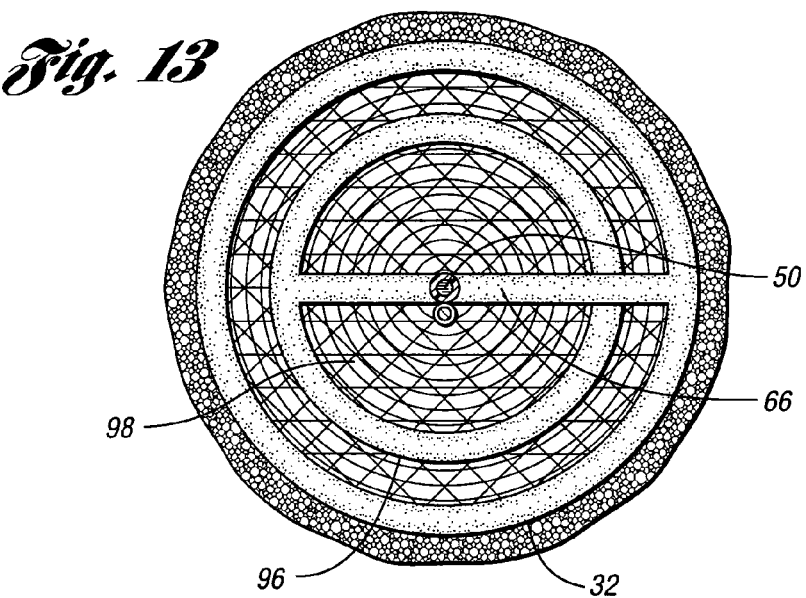
*Fig. 14*
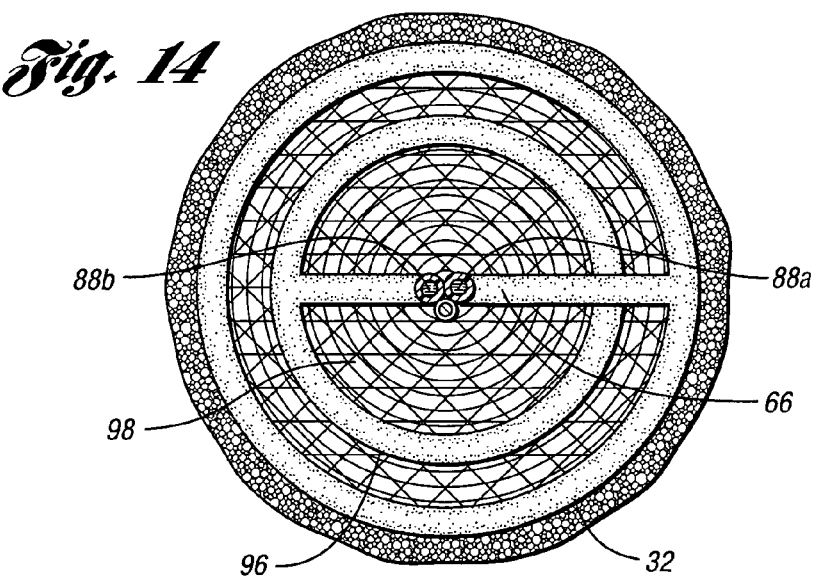

EMBOLIC PROTECTION DEVICE

CROSS-REFERENCE TO RELATED APPLICATION

This application claims benefit of U.S. Provisional Application No. 60/661,731, filed Mar. 15, 2005 entitled Embolic Protection Device.

BACKGROUND

1. Field of the Invention

The invention relates generally to medical devices. More specifically, the invention relates to intravascular distal embolic protection devices.

2. Related Technology

Embolic protection devices are percutaneously placed in a body vessel to prevent emboli from traveling and creating an undesirable embolism, e.g., pulmonary embolism. For example, vena cava filters are used for trapping emboli in the vena cava filter to prevent pulmonary embolism. Also, antiplatelet agents and anticoagulants may be used to breakdown blood clots. Moreover, snares and baskets (e.g., stone retrieval baskets) are used for retrieving urinary calculi. Additionally, occlusion coils are commonly used to occlude aneurysms and accumulate thrombi in a body vessel.

Treatments for a stenotic lesion provide a potential in releasing blood clots and other thrombi plaque in the vasculature of the patient. One example is the treatment for a carotid artery stenosis. Generally, carotid artery stenosis is the narrowing of the carotid arteries, the main arteries in the neck that supply blood to the brain. Carotid artery stenosis (also called carotid artery disease) is a relatively high risk factor for ischemic stroke. The narrowing is usually caused by plaque build-up in the carotid artery.

Carotid angioplasty is a more recently developed treatment for carotid artery stenosis. This treatment uses balloons and/or stents to open a narrowed artery. Carotid angioplasty is a procedure that can be performed via a standard percutaneous transfemoral approach with the patient anesthetized using light intravenous sedation. At the stenosis area, an angioplasty balloon is delivered to predilate the stenosis in preparation for stent placement. The balloon is then removed and exchanged via catheter for a stent delivery device. Once in position, a stent is deployed across the stenotic area. If needed, an additional balloon can be placed inside the deployed stent for post-dilation to make sure the struts of the stent are pressed firmly against the inner surface of the vessel wall. During the stenosis procedure however, there is a risk of such blood clots and thrombi being undesirably released into the blood flow within the vasculature.

Therefore, distal embolic protection devices, such as occlusive devices and filters, have been developed to trap and to prevent the downstream travel of the blood clots and thrombi. The filters are typically advanced downstream of a site that is to be treated and then opened into an opened state to increase the filter area. The blood clots and thrombi can be captured in the opened filter while blood is still able to flow therethrough.

However, filter devices may fail to completely open within the blood vessel, leaving gaps between the filter outer surface and the blood vessel inner surface. These gaps may permit the above-described blood clots and thrombi to flow past the filter, unoccluded. As a result, the unoccluded blood clots and thrombi may thereby compromise the blood flow at a location distal from the treatment site.

Thus, there is a need to improve the opening of the filter device within the blood vessel to effectively capture the unoccluded blood clots and thrombi.

SUMMARY

In one aspect of the present invention, an embolic protection device is provided to collect embolic debris from within a body vessel. Generally, the device includes a filter for collecting embolic debris and a frame for supporting the filter. The frame generally defines a closed loop that has a collapsed state and an opened state. Furthermore, the frame includes a tube portion that receives an opening means to open the closed loop from the collapsed state to the opened state.

In another aspect of the present invention, the closed loop includes a circumferential outer surface that engages the body vessel in a substantially fluid-tight connection when the closed loop is in the opened state. The outer surface defines a substantially circular shape when the closed loop is in the opened state. Generally, the closed loop is substantially torus-shaped in the opened state.

In yet another aspect of the present invention, the device further includes a connecting portion that is in fluid communication with the closed loop. More specifically, the connecting portion is connected to the closed loop and extends away therefrom in a direction that is substantially parallel with a longitudinal axis of the body vessel. The connecting portion may also extend radially away from the closed loop.

In another aspect of the present invention, the device further includes a guide wire that extends along the body vessel longitudinal axis. The guide wire is slidably coupled with the connecting portion such as to permit the device to travel along the longitudinal axis to its desired location within the body vessel.

In yet another aspect of the present invention, the embolic protection device includes a locator device having radiopaque properties. The radiopaque properties of the locator device permit a device user, such as a medical professional, to locate the embolic protection device within a patient's body. Furthermore, the embolic protection device is preferably delivered into the body vessel via a delivery device that receives the closed loop in the collapsed state. More preferably, the delivery device is a catheter.

The present invention may also include a second frame that defines a second closed loop that supports the filter and that is positioned distally of the above-described frame. The second closed loop has a collapsed state and an opened state. More specifically, the second closed loop includes a tube portion for receiving an opening means and for opening the closed loop into the opened state, similarly to the above-described closed loop.

In one aspect of the present invention, the opening means for opening the frame is a fluid that is injected into the tube portion to inflate the closed loop into the opened state. Preferably, the fluid is a saline solution that is injected through the connecting portion and into the frame. The tube portion may each have expandable internal volumes that increase when the fluid is injected therein. Furthermore, the tube portion may be composed of a generally elastic material to further permit the expansion. The fluid may also be used in the above-described design having first and second frames.

In another aspect of the present invention, the opening means for opening the first and second frames is an opening member received by the tube portion to open the closed loop into the opened state. Preferably, the opening member is a wire having an axial stiffness that is substantially greater than its radial stiffness. The stiffness coefficients of the wire permit navigation of the wire through the body vessels. The wire may be a hollow tube to improve the ratio of stiffness coefficients and to minimize part weight. Additionally, in the above-described design having first and second frames, the embolic protection device may include a second opening member that is received by the second frame.

In yet another aspect of the present invention, the frame includes a telescoping portion that is received within a receiving portion of the frame. The telescoping portion is slideable within the receiving portion such as to adjust a radius of the opened state closed loop. More specifically, as the fluid fills the tube portion of the frame and applies a force onto the telescoping portion the frame radially opens towards the blood vessel walls.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIG. 7 is a cross-sectional view taken along line 7-7 in FIG. 6 showing the embolic protection device deflated into the collapsed state;

FIG. 8 is a cross-sectional view taken along line 8-8 in FIG. 6 showing the tube portion of the frame having a decreased internal volume from the substantial removal of the fluid from the tube portion;

FIG. 9 is a cross-sectional view, similar to that shown in FIG. 2, of an alternative design embodying the principles of the present invention, including a wire received within the tube portion to open the frame into the opened state;

FIG. 10 is an enlarged cross-sectional view taken along line 10-10 in FIG. 9, showing the wire received within the tube portion of the frame;

FIG. 11 is an enlarged cross-sectional view similar to that shown in FIG. 9, showing a hollow wire received within the tube portion of the frame;

FIG. 13 is a cross-sectional view taken along line 13-13 in FIG. 12 showing the embolic protection device opened into the opened state by the fluid located within the tube portions of the first and second frames; and FIG. 14 is an enlarged cross-sectional view similar to that shown in FIG. 13, showing a hollow wire received within the tube portions of the first and second frames.

DETAILED DESCRIPTION

Embodiments of the present invention generally provide distal protection devices, distal protection apparatus, and methods for capturing emboli in a body vessel during angioplasty for treatment of a stenosis. One particular stenosis is a carotid artery stenosis. The embodiments solve the concerns of current stenosis treatments, such as the relatively high risks of surgery and the potential release of emboli into the vasculature during the stenosis procedure. Embodiments of the present invention provide a relatively low risk approach to capturing emboli released during a stenosis procedure, e.g., balloon angioplasty.

Figure 1:
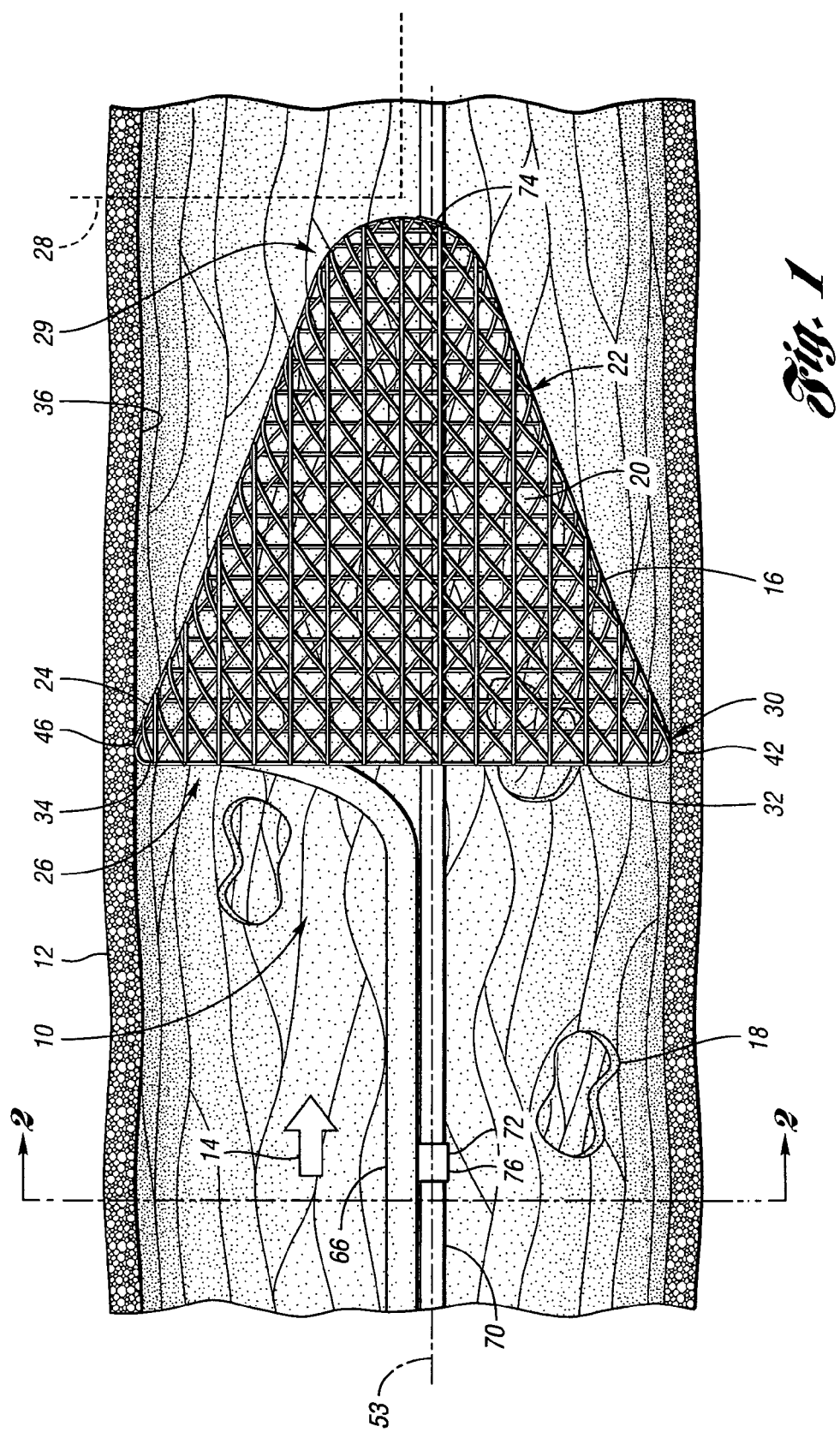
FIG. 1 is an environmental side view of an embolic protection device having a frame and a filter opened into opened states and embodying the principles of the present invention, where the embolic protection device is shown located within a partially cut-away blood vessel.

Referring now to the drawings, FIG. 1 shows an embolic protection device 10 positioned within a body vessel, such as a blood vessel 12 that has a blood flow therethrough in a direction generally indicated by reference numeral 14. The embolic device 10 includes a filter 16 and is positioned downstream of emboli 18, such as blood clots and plaque fragments, to trap and to prevent the downstream travel of the emboli 18, thereby reducing the likelihood of an embolism or of the downstream blood vessels becoming blocked. As will be discussed in more detail below, the filter 16 operates similarly to a sieve, having openings 20 that permit blood to flow therethrough while preventing the emboli 18 from doing the same.

The filter 16 is composed of a mesh or a web-like material 22, but any suitable material may be used. More specifically, the filter material 22 is preferably strong enough to avoid rupture during use and thin enough to conveniently fit within the blood vessel 12. Furthermore, the filter material 22 is preferably sufficiently flexible such that the filter 16 is able to conform to various shapes and configurations, as may be needed to properly engage the blood vessel 12.

The filter 16 includes a proximally-located mouth portion 24 that is substantially opened to an opened state 26 for receiving the emboli 18. Preferably, the embolic device 10 forms a substantially fluid-tight seal 30 with the blood vessel when the mouth portion 24 is in the opened state 26. The seal 30 may be formed by the mouth portion, the filter 16, or both. The seal 30 prevents emboli 18 from flowing around the filter 16 and from potentially causing the above-described conditions.

The filter 16 further includes a tail portion 29 located distally of the mouth portion 24. The tail portion 29 is substantially closed, such as to permit blood to flow through the openings 20, while simultaneously preventing emboli 18 from doing the same. Therefore, the emboli 18 are collected within the tail portion 29.

Figure 5:
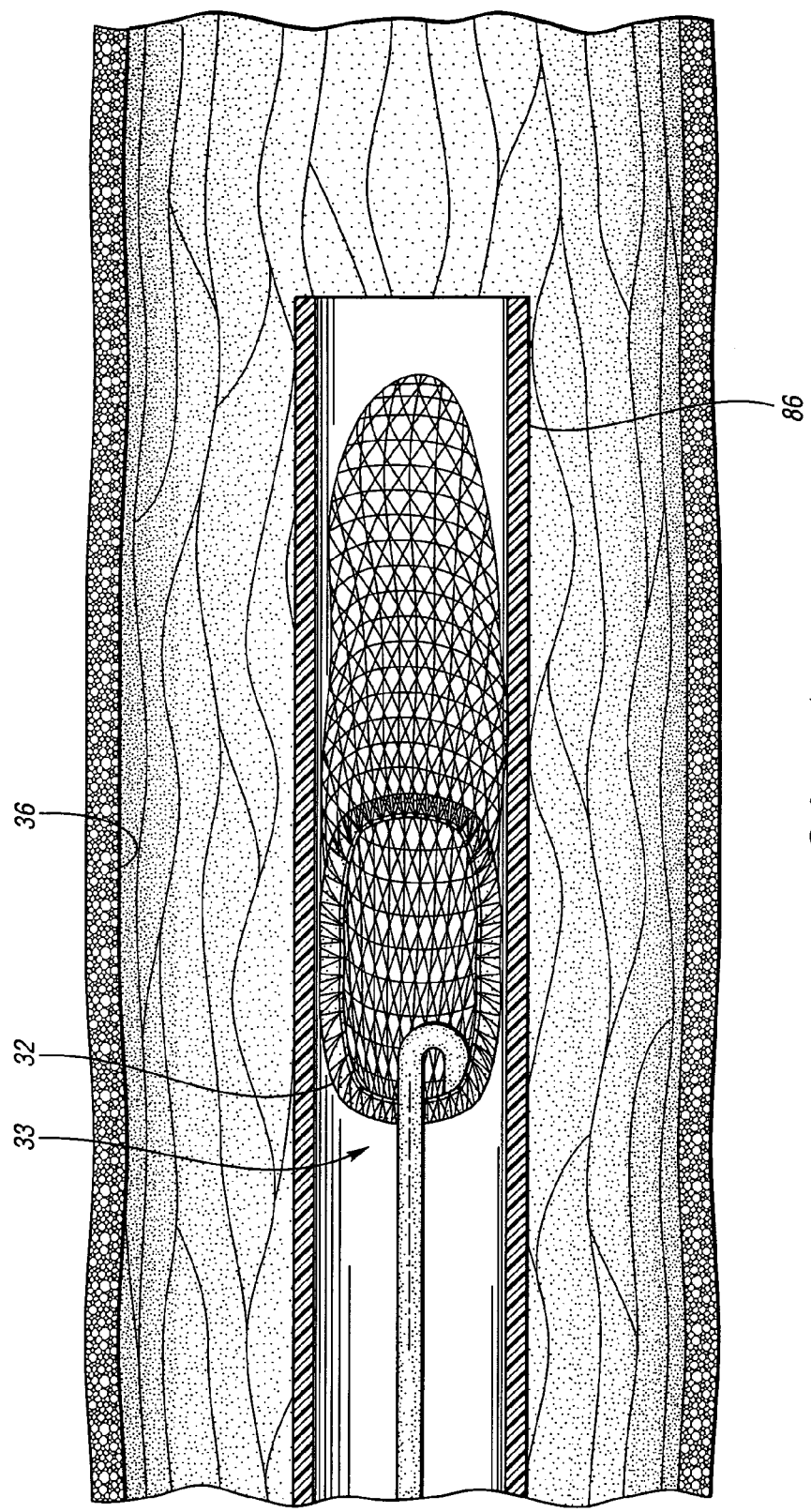
FIG. 5 is a plan view of the embolic protection device positioned within a delivery device, where the frame is deflated into a collapsed state from the substantial removal of the fluid from the tube portion.
Figure 6:
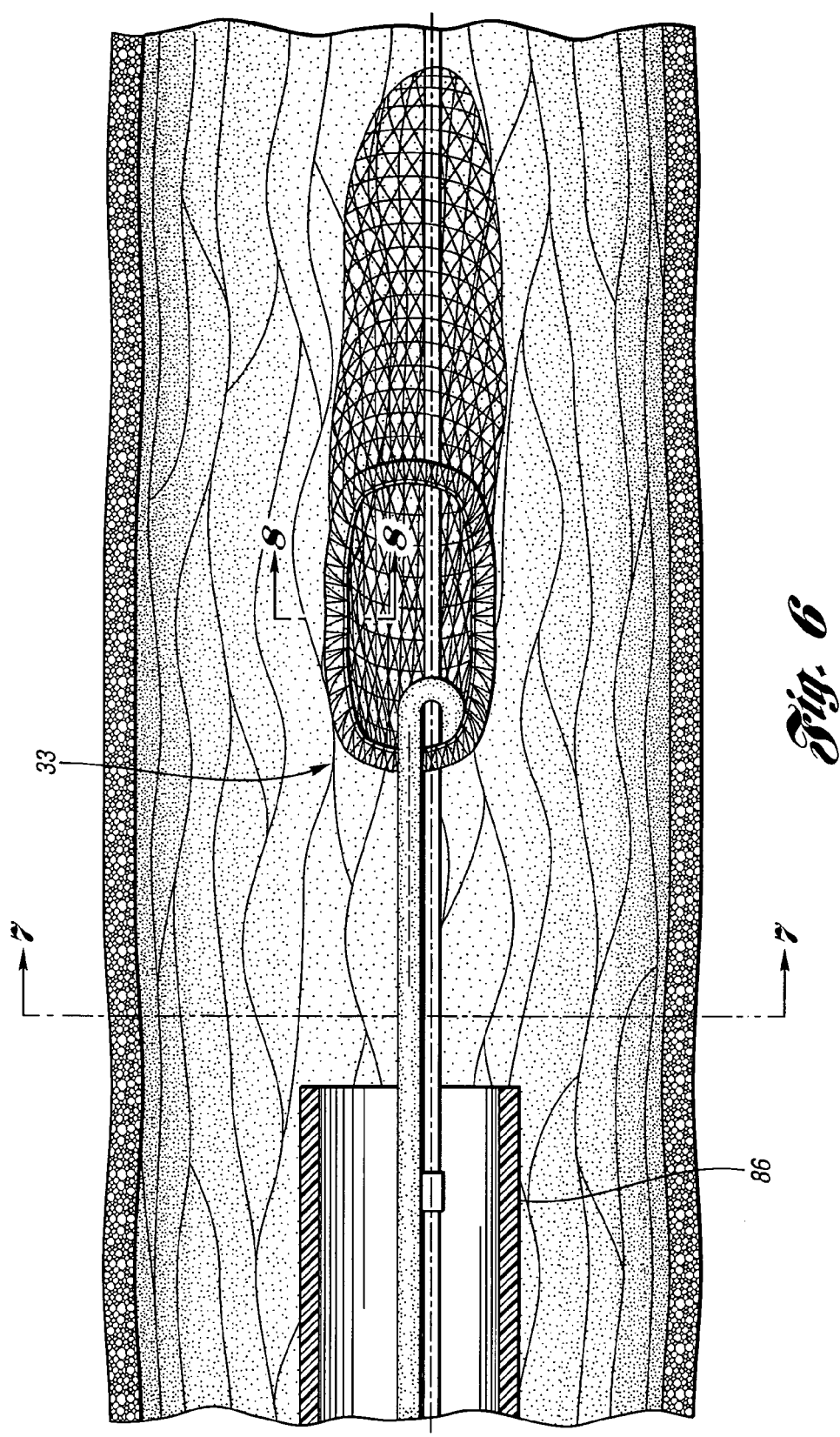
FIG. 6 shows a plan view of the embolic protection device deployed from the delivery device, where the frame is deflated into the collapsed state.

The mouth portion 24 is held in the opened state 26 by a frame 32 that extends around the perimeter of the mouth portion 26. The frame 32 is collapsible into a collapsed state 33, as shown in FIGS. 5 and 6, such as to permit blood flow 14 between the frame 32 and the blood vessel inner walls 36. As will be discussed in more detail below, the frame 32 is typically in the collapsed state 33 while delivering the device 10 into a desired location of the blood vessel 12 and while removing the device 10 from the desired location. The frame 32 is preferably composed of a flexible material such as plastic or of a compliant material such as rubber. Alternatively, the frame 32 is composed of a plurality of generally rigid sections that are movable with respect to each other. Additionally, any sufficient collapsible design that permits delivery of the device 10 into the blood vessel 12 may be used.

Figure 2:
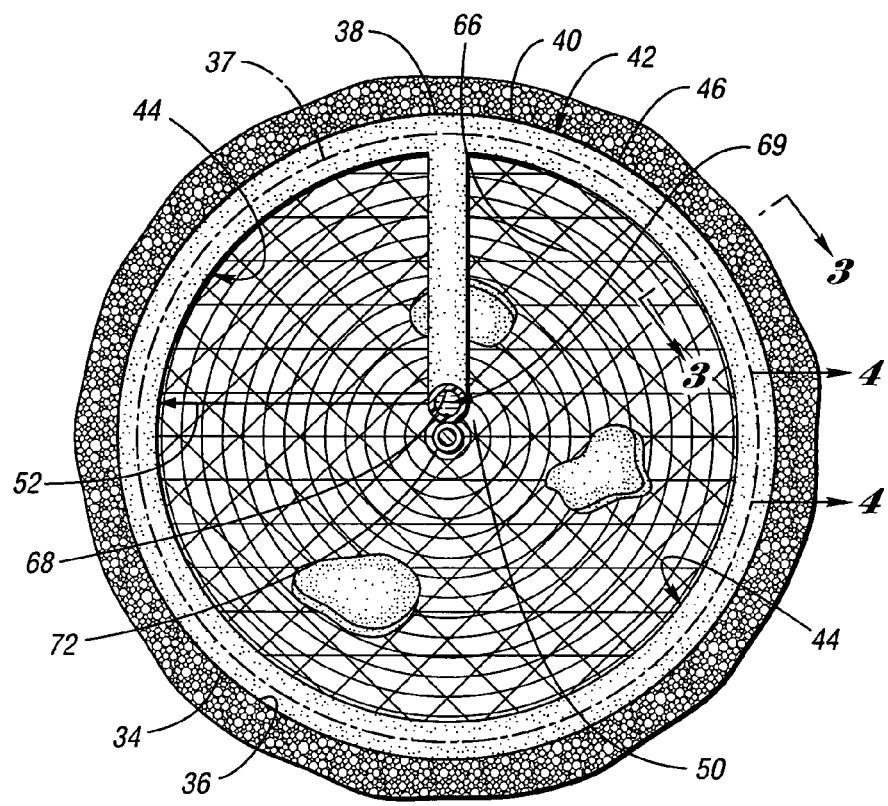
FIG. 2 is a cross-sectional view taken along line 2-2 in FIG. 1 showing the embolic protection device opened into the opened state by a fluid located within a tube portion of the frame.

The frame 32 forms an annular closed loop 34 that is positioned within the filter 16 to open the mouth portion 24 towards an inner wall 36 of the blood vessel 12. Alternatively, the filter 16 may be connected to the radially inner surface of the closed loop 34. A first portion 38 of the frame 32 is connected to a second portion 40 of the frame such that the closed loop 34 defines a continuous path 37. The closed loop 34 shown in FIG. 2 is generally circular, but any suitable shape and size may be used. The first and second portions 38, 40 are connected by any suitable means, such as by welding, adhesives, bonding (such as through heat treatment), or mechanical fasteners. Alternatively, the frame 32 is a single, unitary component.

The closed loop 34 design improves the seal 30 between the frame 32 and the blood vessel 12. More specifically, a free, unconnected portion of the frame would be able to freely flow downstream rather than tightly engaging the blood vessel 12.

The closed loop 34 includes an outer circumferential surface 42 that forms the substantially fluid-tight seal 30 with the blood vessel 12 when the frame 32 is in the opened state 26. The inner walls 36 of blood vessels 12 typically have a generally circular cross-section. Therefore, to effectively form the substantially fluid-tight seal 30, the outer surface 42 of the closed loop 34 also has a generally circular shape when the frame 32 is in the opened state 26. Furthermore, the closed loop 34 includes an inner circumferential surface 44 corresponding to the shape of the outer circumferential surface 42 such that the opened state 26 closed loop 34 is substantially torus-shaped.

The closed loop 34 is able to open to the opened state 26 by receiving an opening means. More specifically, the closed loop 34 is defined by a tube 46 having a tube portion 48 that defines an internal volume 49 and that is able to receive the opening means. The opening means may be any fluid or solid component that is suitable for opening the closed loop 34 in the radial direction 28. Acceptable fluids include, but are not limited to, saline and water, and acceptable solids include, but are not limited to, a wire and a tube.

Figure 3:
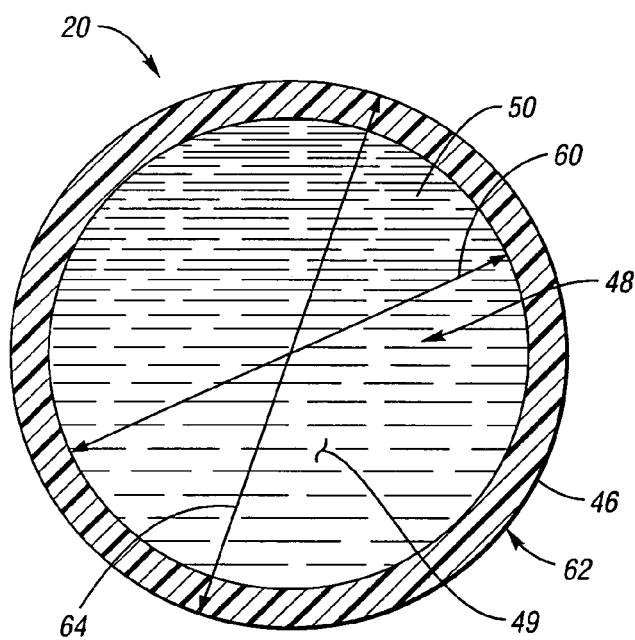
FIG. 3 is a cross-sectional view taken along line 3-3 in FIG. 2, showing the fluid located within the tube portion of the frame.

In one design, shown in FIGS. 2 and 3, the opening means is a fluid 50 located within the tube portion 48 that causes the closed loop 34 to open in the radial direction 28. More specifically, as the tube portion 48 of the closed loop 34 fills with the fluid 50, the circumferential length of the closed loop 34 along the path 37 is maximized, thereby causing the radius 52 of the closed loop 34 to increase. The fluid 50 shown in the Figures is a saline solution, but any suitable fluid may be used.

The medical professional using the embolic protection device 10 is able to position the closed loop 34 by controlling the radius 52 of the closed loop 34 via a connecting portion 66 extending away from the closed loop 34. More specifically, the connecting portion 66 shown in FIGS. 1-4 includes a lumen 68 that receives the fluid 50 and that is in fluid communication with the closed loop 34 tube portion 48. Therefore, the medical professional is able to inject the fluid into the closed loop 34 via the connecting portion 66. The connecting portion 66 shown in the Figures includes a first portion generally intersecting a centerpoint 69 of the frame 32 and a second portion extending radially from the first portion to connect to the closed loop 34. Alternatively, the connecting portion 66 may be radially off-set from the centerpoint 69. In another design, the frame 32 includes a valve (not shown) to force the connecting portion 66 to inflate or open.

The connecting portion 66 and the frame 32 preferably each have shape memory such as to naturally conform to a desired position when in the opened state 26. More specifically, the connecting portion 66 and frame 32 are preferably positioned substantially perpendicular to each other such that a plane defined by the frame 32 is normal to the connecting portion 66 or are connected by a curved portion that generally connects two perpendicular portions. This configuration improves the seal 30 between the frame 32 and the blood vessel 12 because it urges the frame 32 to lie along a plane that is perpendicular to a longitudinal axis 53 of the blood vessel 12. Stated another way, the plane of the closed loop is preferably non-parallel to the longitudinal axis 53 of the blood vessel 12 and is most preferably perpendicular to the longitudinal axis 53.

Blood vessels 12 typically vary significantly in size and in shape. Therefore the radius 52 of the opened state 26 frame is preferably variable to effectively form the seal 30. More specifically, the frame 32 preferably includes a mechanism that permits the variation of the opened state radius 52.

Figure 4:
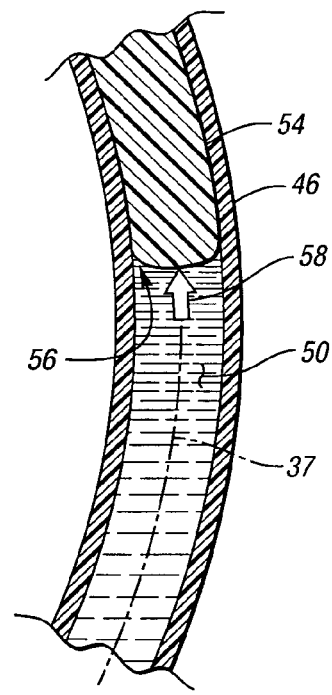
FIG. 4 is a cross-sectional view taken along line 4-4 in FIG. 2, showing a telescoping portion of the frame being received within a receiving portion of the frame.

Referring to FIG. 4, one such mechanism is a telescoping portion 54 slidably received within the tube 46 to permit variation of the opened state radius 52. The telescoping portion 54 forms a generally fluid-tight seal 56 with the inner surface of the tube 46 to prevent the fluid 50 from flowing between the respective components 54, 46. As a result, when the tube 46 becomes filled with fluid, a force 58 is applied onto he telescoping portion 54. The force 58 causes the telescoping portion 54 to move along the path 37, thereby increasing the circumferential length and the opened state radius 52 of the frame 32.

The telescoping portion 54 and/or the tube 46 may include a hard stop mechanism (not shown) that prevents the circumferential length from expanding beyond a particular size. More specifically, the hard stop mechanism prevents the telescoping portion 54 from exiting the tube 46. During operation of the embolic protection device 10, the telescoping portion 54 will stop moving when the force 58 from the fluid flow is generally equal to a force between the expanding tube 46 and the blood vessel inner wall 36. Furthermore, the telescoping portion 54 will also stop moving when the hard stop is engaged. The hand stop is preferably positioned so that the closed loop 34 is able to expand to form the seal 30 before the hand stop is engaged.

Referring back to FIG. 3, another mechanism for varying the opened state 26 closed loop radius 52 is a variable internal diameter 60 of the tube 46. For example, as shown in FIG. 3, the tube may be composed of an elastic material 62 such that the internal diameter 60 of the tube 46 is expandable. Therefore, when an increased volume of the fluid 50 is inserted within the tube 46, the internal diameter 60 and an external diameter 64 of the tube 46 increase and cause the opened state 26 closed loop radius 52 to increase. The closed loop 34 in this design may define a continuous fluid flow path along the path 37 such that the first portion 38 and the second portion 40 are in fluid connection with each other.

The medical professional using the embolic protection device 10 is also able to control the position of the embolic protection device 10 via a guide wire 70 and a connecting sleeve 72. More specifically, the connecting portion 66 is connected to the connecting sleeve 72, which slidably receives the guide wire 70. Therefore, the embolic protection device 10 is able to travel through the blood vessels in a direction generally parallel to the guide wire 70. The guide wire 70 intersects the filter 16 adjacent to the tail portion 29 thereof, which preferably includes a sealing component 74 to permit sliding movement between the filter 16 and the guide wire 70 while preventing emboli 18 from flowing therebetween.

The connecting sleeve 72 also preferably includes a locator device having radiopaque properties to permit the medical professional to more effectively track the location of the device 10 within the blood vessels 12. More specifically, the connecting sleeve 72 includes a coating of radiopaque material 76 that is visible through the patient's body with the assistance of detection equipment. The locator device is particularly beneficial during the delivery of the embolic protection device 10 into the desired location of the blood vessel 12 and during the removal of the device 10 from the same.

Referring now to FIGS. 1-3 and 6-8, the details of the opened state 26 and the collapsed state 33 will now be discussed in more detail. Preferably, the closed loop 34 has the opened state radius 52 (FIG. 2) when in the opened state 26 and a closed state radius 80 (FIG. 7) when in the collapsed state 33. As discussed above, the opened state radius 52 is substantially equal to that of the blood vessel 12, while the closed state radius 80 is substantially smaller than that of the blood vessel 12. Therefore, when the frame 32 is in the collapsed state 33 a gap 82 is present between the frame 32 and the blood vessel 12, permitting the embolic protection device 10 to travel through the blood vessel 12 as desired. As also discussed above, the collapsed state 33 is particularly desirable during the delivery the embolic protection device 10 into the desired location of the blood vessel 12 and during the removal of the device 10 from the same.

Furthermore, if the frame 32 is made of an elastic material, the internal volume of the closed loop may also vary as the opening means is inserted into the tube portion 48. The tube portion 48 defines the first internal volume 49 (FIG. 3) when the frame 32 is in the opened state 26 and a second internal volume 84 (FIG. 8) when in the collapsed state 33. The first internal volume 49 is preferably substantially greater than the second internal volume 84 due to the fluid 50 located within the tube portion 48 during the opened state 26. More specifically, the varying internal volume may occur for one or both of the following reasons. First, the fluid 50 is preferably removed from within the tube portion 48 when the frame is in the collapsed state 33, thereby creating a partial vacuum and a reduced volume within the tube portion 48 during this state 33. Secondly, the fluid 50 preferably causes expansion of the compliant walls of the tube 26 during the opened state 26, thereby increasing the first internal volume 49. When the frame 32 is in the collapsed state 33, all or a substantial portion of the air is also removed from the tube portion 48 so that the tube portion 48 can be more easily filled and also to minimize or prevent air from entering the blood vessel 12 in the case of a ruptured tube portion 48.

Referring now to FIGS. 5 and 6, the procedure for deployment of the embolic protection device 10 will now be discussed in more detail. The embolic protection device 10 preferably includes a delivery device, such as a catheter 86, for positioning the embolic protection device 10 within the blood vessel 12 at the desired location. More specifically, as shown in FIG. 5, the catheter 86 is inserted into the blood vessel 12 at a location downstream of the emboli 18 while the embolic protection device 10 is located within the catheter 86 in the collapsed state 33. Then, as shown in FIG. 6, the embolic protection device 10 remains in the collapsed state 33 and is released from the catheter 86 and is permitted to flow along the blood stream to its desired location. Next, the catheter 86 is removed from the blood vessel 12 and the embolic protection device 10 is opened into the opened state 26 by the medical professional. Alternatively, the catheter 86 remains within the blood vessel 12 after the deployment of the embolic protection device 10, as is the case with many catheters that are configured to deploy balloon catheter along with the embolic protection device 10.

In another design, shown in FIGS. 9-11, the opening means is an opening member, such as a wire 88, located within the tube portion 48 that causes the closed loop 34 to open in the radial direction 28. More specifically, the wire 88 is fed into the tube portion 48 to cause the closed loop 34 to open in the radial direction 28. The wire 88 preferably has an axial stiffness in the axial direction 90 that is greater than its radial stiffness in the radial direction 92 to permit the wire 88 to negotiate the bending path through the tube 46. Furthermore, as shown in FIG. 11, the opening member may be a hollow tube 94 to decrease the radial stiffness in the radial direction 92' and to reduce component weight and cost.

In this embodiment, the tube portion 48 of the connecting portion 66 also preferably receives the wire 88. Furthermore, the connecting portion 66 and the closed loop 34 are connected to each other such that the medical professional can easily feed the wire 88 through the connecting portion 66 and into the closed loop 34.

Additionally, this embodiment may include a mechanism that permits the variation of the opened state radius 52. More specifically, the device 10 may include the telescoping portion 54 slidably received within the tube 46 to permit variation of the opened state radius 52. However, instead of being moved forward by a fluid force, the telescoping portion 54 in this embodiment is driven forward by the wire 88. Alternatively, the device 10 may include the tube 46 having a flexible internal diameter 60. However, instead of being radially opened by fluid pressure, the internal diameter 60 is increased by the wire 88 having a larger diameter than the tube 46.

Figure 12:
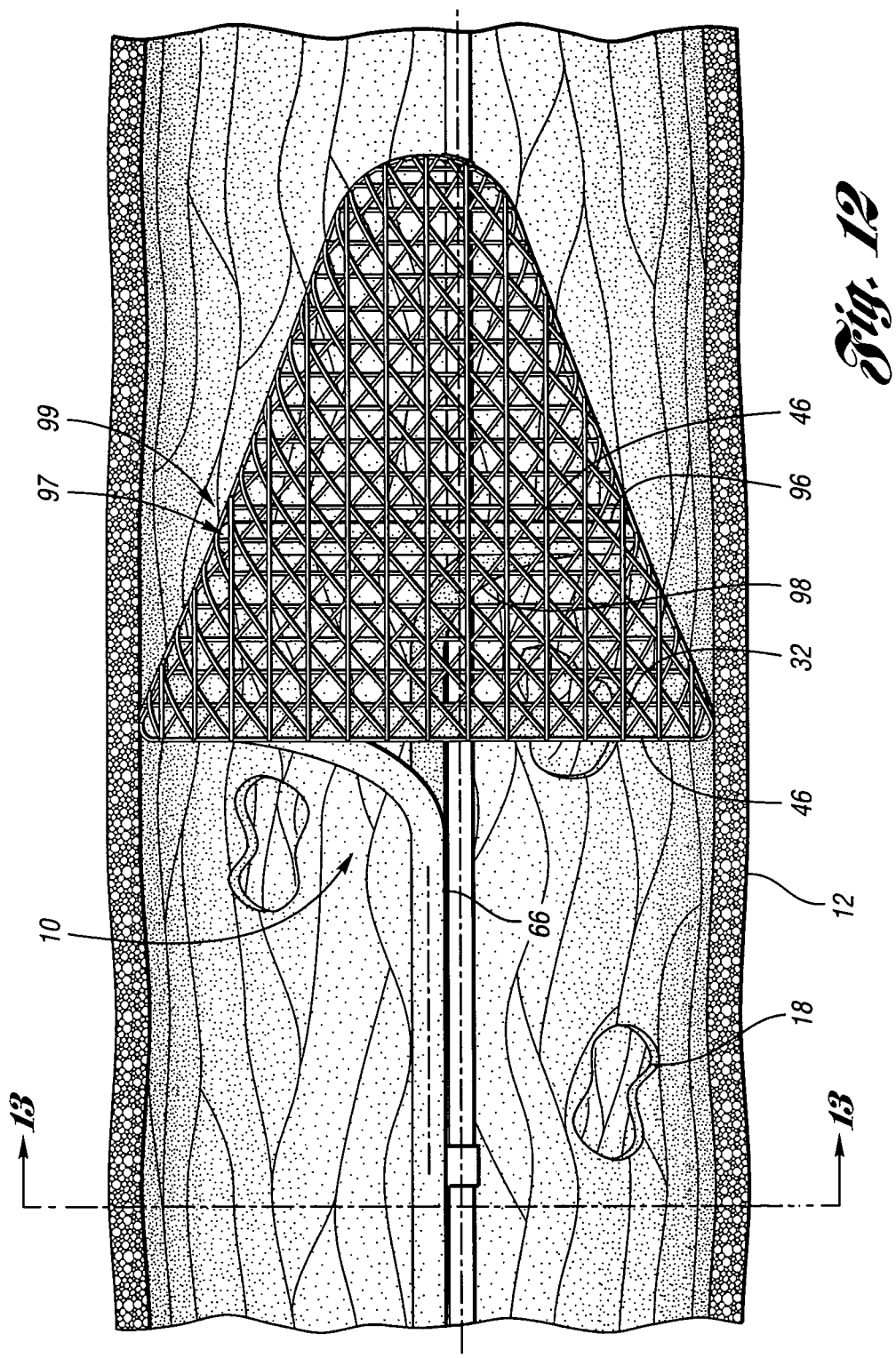
FIG. 12 is a plan view of an embolic protection device, similar to that shown in FIG. 1, of an alternative design embodying the principles of the present invention, including first and second frames opened into an opened state to open the filter.

Referring now to FIGS. 12-14, another embodiment of the present invention will now be discussed. More specifically, the embolic protection device 10 in FIG. 12 includes a second frame 96 defining a second closed loop 97 having a collapsed state (not shown) and an opened state 99 similar to the frame 32 described above. Furthermore, the second frame 96 is connected to a second connecting portion 98.

The first and second frames 32, 96 of the embolic protection device 10 shown in FIGS. 12 and 13 are opened into the respective opened states 26, 99 by the fluid 50 located within the tube portions of the tubes 46. In this design, the respective connecting portions 66, 98 of the respective frames 32, 96 are both in fluid communication with each other such that the medical professional can control the inflation of both frames 32, 96 simultaneously. Alternatively, other suitable designs may be used.

The first and second frames 32, 96 of the embolic protection device 10 shown in FIG. 14 are opened into the respective opened states 26, 99 by the wires 88a, 88b located within the tube portions of the tubes 46. In this design, the respective connecting portions 66, 98 of the respective frames 32, 96 are not internally connected with each other so the two wires 88a, 88b can be used to independently control the inflation of both frames 32, 96. Alternatively, other suitable designs may be used.

It is therefore intended that the foregoing detailed description be regarded as illustrative rather than limiting, and that it be understood that it is the following claims, including all equivalents, that are intended to define the spirit and scope of this invention.

What is claimed is:

1. An embolic protection device for collecting embolic debris within a body vessel having an inner wall, the embolic protection device comprising:

a tubular frame having a lumen and a longitudinal axis, wherein a portion of the frame forms an annular closed loop having a collapsed state and an opened state;

a telescoping portion having an end and being slidably received within the lumen of the closed loop of the frame to open the closed loop from the collapsed state to the opened state;

a connecting portion including a first portion radially connected to the tubular frame and a second portion extending from the first portion to connect to the closed loop, the second portion being disposed coaxially with the tubular frame, the first portion being radially off-set from the centerpoint; and a filter connected to the frame to collect the embolic debris, the filter having a proximally located mouth portion, the annular closed loop being positioned within the filter to open the mouth portion towards the inner wall of the body vessel;

wherein a radius of the opened state closed loop is adjustable based on a force applied to the end the telescoping portion by a fluid within the lumen of the frame, the force moving the telescoping portion along the longitudinal axis of the tubular frame with the fluid flowing from the connecting portion to the tubular frame.

2. An embolic protection device as in claim 1, wherein the closed loop includes a first radius measured perpendicularly to a longitudinal axis of the body vessel when the closed loop is in the collapsed state and having a second radius measured perpendicularly to the longitudinal axis when the closed loop is in the opened state, wherein the second radius is greater than the first radius.

3. An embolic protection device as in claim 1, wherein the closed loop includes a circumferential outer surface engaging the body vessel in a fluid-tight connection when the closed loop is in the opened state.

4. An embolic protection device as in claim 1, wherein the closed loop is torus-shaped when the closed loop is in the opened state.

5. An embolic protection device as in claim 1, wherein the connecting portion is in fluid communication with and extending away from the closed loop.

6. An embolic protection device as in claim 5, further comprising a guide wire slidably coupled with the connecting portion.

7. An embolic protection device as in claim 6, further comprising a locator device having radiopaque properties that is coupled with the closed loop.

8. An embolic protection device as in claim 5, further comprising a delivery device that receives the closed loop in the collapsed state.

9. An embolic protection device as in claim 1, further comprising a second frame defining a second closed loop having a collapsed state and an opened state, wherein the second frame is located distally of the frame.

10. An embolic protection device for collecting embolic debris within a body vessel having an inner wall, the embolic protection device comprising:

a tubular frame having a centerpoint, a lumen, and a longitudinal axis, wherein a portion of the frame forms an annular closed loop having a collapsed state and an opened state, the lumen configured to receive a fluid to inflate the closed loop into the opened state;

a connecting portion including a first portion radially connected to the tubular frame and a second portion disposed coaxially with the tubular frame, the first portion being one of generally intersecting the centerpoint and radially off-set from the centerpoint; and a filter connected to the frame to collect the embolic debris, the filter having a proximally located mouth portion, the annular closed loop being positioned within the filter to open the mouth portion towards the inner wall of the body vessel;

the frame including a telescoping portion having an end and being slidably received within the lumen of the closed loop such that a radius of the opened state closed loop is adjustable based on a force applied to the end the telescoping portion by the fluid that flows from the connecting portion to the tubular frame, the force moving the telescoping portion along the longitudinal axis of the tubular frame.

11. An embolic protection device as in claim 10, wherein the tubular frame includes a tube portion, the tube portion of the frame defines a first internal volume when the closed loop is in the collapsed state, the tube portion of the frame defines a second internal volume when the closed loop is in the opened state, and the second internal volume is greater than the first internal volume.

12. An embolic protection device as in claim 10, wherein the tube portion is composed of an elastic material.

13. An embolic protection device as in claim 10, wherein the connecting portion is in fluid communication with and extends away from the closed loop, wherein the tube portion defines a continuous flow path around the closed loop and wherein the flow path is in fluid communication with the connecting portion.

14. An embolic protection device as in claim 10, further comprising a second frame defining a second closed loop having a collapsed state and an opened state, wherein the second frame is located distally of the frame, and wherein the filter is connected to the frame and the second frame.

15. An embolic protection device for collecting embolic debris within a body vessel, the embolic protection device comprising:

a tubular frame having a lumen and a longitudinal axis, wherein a portion of the frame forms an annular closed loop having a collapsed state and an opened state, the lumen of the frame configured to receive a fluid;

a connecting portion including a first portion radially connected to the tubular frame and a second portion disposed coaxially with the tubular frame, the first portion being one of generally intersecting the centerpoint and radially off-set from the centerpoint; and an opening member having an end and being received by the lumen of the closed loop of the frame to open the closed loop into the opened state based on a force applied to the end of the opening member by the fluid that flows from the connecting portion to the tubular frame, the force moving the opening member along the longitudinal axis of the tubular frame; and a filter coupled with the closed loop to collect the embolic debris, the filter having a proximally located mouth portion, the annular closed loop being positioned within the filter to open the mouth portion towards the inner wall of the body vessel.

16. An embolic protection device as in claim 15, wherein the opening member includes a wire.

17. An embolic protection device as in claim 1, wherein the telescoping portion forms a fluid-tight seal with an inner surface of the tubular frame.

18. An embolic protection device as in claim 1, further comprising a hard stop mechanism that prevents the telescoping portion from exiting the receiving portion.

19. An embolic protection device as in claim 10, wherein the telescoping portion forms a fluid-tight seal with an inner surface of the tubular frame.

20. An embolic protection device as in claim 15, wherein the opening member forms a fluid-tight seal with an inner surface of the tubular frame.

21. The device of claim 10 wherein the second portion extends radially from the first portion when the first portion generally intersects the centerpoint.

* * * * *

UNITED STATES PATENT AND TRADEMARK OFFICE
CERTIFICATE OF CORRECTION

| | | |
|---|---|---|
| PATENT NO. | : 8,945,169 B2 | Page 1 of 1 |
| APPLICATION NO. | : 11/375328 | |
| DATED | : February 3, 2015 | |
| INVENTOR(S) | : Dharmendra Pal | |

It is certified that error appears in the above-identified patent and that said Letters Patent is hereby corrected as shown below:

In the Claims

In column 9, claim 1, line 20, after "applied to the end" insert --of--.

In column 10, claim 10, line 9, after "applied to the end" insert --of--.

Signed and Sealed this
First Day of December, 2015

Michelle K. Lee
*Director of the United States Patent and Trademark Office*